(12) United States Patent
Bartlett et al.

(10) Patent No.: US 8,299,027 B2
(45) Date of Patent: Oct. 30, 2012

(54) METHOD OF MODULATING CELL SURVIVAL AND REAGENTS USEFUL FOR SAME

(75) Inventors: Perry Francis Bartlett, Carlton North (AU); Elizabeth Jane Coulson, Clifton Hill (AU); Katrina Fieldew, Box Hill North (AU); Manuel Baca, Ivanhoe (AU); Trevor Kilpatrick, Parkville (AU); Cheema Surindar, Donvale (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 12/885,194

(22) Filed: Sep. 17, 2010

(65) Prior Publication Data

US 2011/0172143 A1 Jul. 14, 2011

Related U.S. Application Data

(60) Division of application No. 10/921,065, filed on Aug. 18, 2004, now Pat. No. 7,919,471, which is a continuation of application No. 09/821,831, filed on Mar. 30, 2001, now abandoned, which is a continuation of application No. PCT/AU99/00860, filed on Oct. 5, 1999.

(30) Foreign Application Priority Data

Oct. 6, 1998 (AU) .......................................... PP6353
Oct. 7, 1998 (AU) .......................................... PP6351
Jun. 1, 1999 (AU) .......................................... PQ0701

(51) Int. Cl.
A61K 38/18 (2006.01)
(52) U.S. Cl. ...................... 514/8.3; 514/21.5
(58) Field of Classification Search ........................ None
See application file for complete search history.

(56) References Cited

U.S. PATENT DOCUMENTS 5,606,023 A 2/1997 Chen et al.
7,919,471 B2 4/2011 Bartlett et al.

FOREIGN PATENT DOCUMENTS

AU 772811 4/2000
EP 1 121 434 B1 9/2008
WO WO 97/06251 2/1997

OTHER PUBLICATIONS

Rudinger, In "Peptide Hormones" (ed. J.A. Parsons), University Park Press, Baltimore, pp. 1-17 (1976).*
Bamji, S.X., et al., "The p75 Neurotrophin Receptor Mediates Neuronal Apoptosis and is Essential for Naturally Occurring Sympathetic Neuron Death," Journal of Cell Biology 140(4): 911-923 (1998).
Barrett, G.L., et al., "The Low-Affinity Nerve Growth Factor Receptor $p75^{NGFR}$ Mediates Death of PC12 Cells After Nerve Growth Factor Withdrawal," Journal of Neuroscience Research 45: 117-128 (1996).
Barrett, G.L., et al., "The p75 Nerve Growth Factor Receptor Mediates Survival or Death Depending on the Stage of Sensory Neuron Development," Proc. Natl. Acad. Sci. USA 91(14): 6501-6505(1994).
Bavec, A., et al., "Structural Features of Amphipathic Peptides Required for the Activation of G-Proteins," Acta Chim. Slov., 45(1):27-34 (1998).
Cheema, S.S., et al., "Reducing p75 Nerve Growth Factor Receptor Levels Using Antisense Oligonucleotides Prevents the Loss of Axotomized Sensory Neurons in the Dorsal Root Ganglia of Newborn Rats," Journal of Neuroscience Research 46: 239-245 (1996).
Conner, J.M., et al., "The Localization of Nerve Growth Factor-Like Immunoreactivity in the Adult Rat Basal Forebrain and Hippocampal Formation," Journal of Comparative Neurology 319: 454-462 (1992).
Coulson, E.J., et al., "Chopper, a New Death Domain of the p75 Neurotrophin Receptor That Mediates Rapid Neuronal Cell Death," J. Biol Chem 275(39): 30537-30545 (Sep. 29, 2000).
Coulson, E.J., et al., "p75 Neurotrophin Receptor-Mediated Neuronal Death Is Promoted by Bcl-2 and Prevented by Bcl-$x_L$," J. Biol. Chem., 274(23):16387-16391 (1999).
De Simone, R., et al., "mRNA for NGF and p75 in the Central Nervous System of Rats Affected by Experimental Allergic Encephalomyelitis," Neuropathy & Applied Neurobiology 22: 54-59 (1996).
Hileman, M.R., "A Cytoplasmic Peptide of the Neurotrophin Receptor p75NTR: Induction of Apoptosis and NMR Determined Helical Conformation," FEBS Letters 415: 145-154 (1997).
Lee, T.-H., et al., "Expressions of Nerve Growth Factor and p75 Low Affinity Receptor After Transient Forebrain Ischemia in Gerbil Hippocampal CA1 Neurons," Journal of Neuroscience Research 41: 684-695 (1995).
Levi-Montalcini, R., "Developmental Neurobiology and the Natural History of Nerve Growth Factor," Ann. Rev. Neurosci. 5: 341-362 (1982).
Liepinsh, E., et al., "NMR Structure of the Death Domain of the p75 Neurotrophin Receptor," EMBO J. , 16(16):4999-5005 (1997).
Longo, F.M., et al., "Synthetic NGF Peptide Derivatives Prevent Neuronal Death via a p75 Receptor-Dependent Mechanism," Journal of Neuroscience Research, 48: 1-17 (1997).

(Continued)

Primary Examiner — Robert C Hayes
(74) Attorney, Agent, or Firm — Hamilton, Brook, Smith & Reynolds, P.C.

(57) ABSTRACT

The present invention relates generally to a method for modulating cell survival. Modulation of cell survival includes inducing, enhancing or otherwise promoting cell survival such as the survival of neural cells as well as facilitating cell death such as the death of targeted cancer cells. The modulation of cell survival is mediated by a region identified on the p75 neurotrophin receptor ($p75^{NTR}$) required for death signalling. The present invention further provides genetic molecules which encode the death signalling region of $p75^{NTR}$ which are useful in antagonising death signal function as well as promoting cell death when expressed in targeted cells. The present invention also contemplates recombinant peptides, polypeptides and proteins as well as chemical equivalents, derivatives and homologues thereof which comprise the death signalling portion of $p75^{NTR}$. Particularly useful molecules of the present invention comprise peptides corresponding to soluble forms of the death signalling portion of $p75^{NTR}$. These molecules antagonise $p75^{NTR}$-mediated cell death.

4 Claims, 9 Drawing Sheets

OTHER PUBLICATIONS

Majdan, M., et al., "Transgenic Mice Expressing the Intracellular Domain of the p75 Neurotrophin Receptor Undergo Neuronal Apoptosis," *Journal of Neuroscience* 17(18): 6988-6998 (1997).

Moix, L.J., et al., "Separate Signals Mediate Hypoglossal Motor Neuron Response to Axonal Injury," *Brain Research* 564: 176-180 (1991).

Nataf, S., et al., "Low Affinity NGF Receptor Expression in the Central Nervous System During Experimental Allergic Encephalomyelitis," *Journal of Neuroscience Research* 52: 83-92 (1998).

Needleman, S.B., et al., "A General Method Applicable to the Search for Similarities in the Amino Acid Sequence of Two Proteins," *J. Mol. Biol.* 48: 443-453 (1970).

Rabizadeh, S., et al., "Induction of Apoptosis by the Low-Affinity NGF Receptor," *Science* 261: 345-348 (1993).

Radeke, M.J., et al., "Gene Transfer and Molecular Cloning of the Rat Nerve Growth Factor Receptor," *Nature* 325: 593-597 (1987).

Rende, M., et al., "Axotomy Induces a Different Modulation of Both Low-Affinity Nerve Growth Factor Receptor and Choline Acetyltransferase Between Adult Rat Spinal and Brainstem Motoneurons," *Journal of Comparative Neurology* 363: 249-263 (1995).

Schwarze, S.R., et al., "In Vivo Protein Transduction: Delivery of a Biologically Active Protein into the Mouse," *Science* 285: 1569-1572 (1999).

Seeburger, J.L., et al., "Spinal Cord Motoneurons Express $p75^{NGFR}$ and $p145^{trkB}$ mRNA in Amyotrophic Lateral Sclerosis," *Brain Research* 621: 111-115 (1993).

Sequence of nerve growth factor receptor mRNA, complete coding sequence (*Homo sapiens*); GenBank Accession No. M14764; version 1; GI:189205; Submitted by M. Bothwell; Last updated Jun. 7, 1995; First available Oct. 26, 1992.

Sequence of nerve growth factor receptor protein (*Homo sapiens*); GenPept Accession No. AAB59544; version 1; GI:189205; Submitted by M. Bothwell; Last updated Jun. 7, 1997; First available Oct. 26, 1992.

Sequence of rat (*Rattus norvegicus*) mRNA for fast nerve growth factor receptor (NGFR); GenBank Accession No. X05137; version 1; GI:56755; Submitted by T.P. Misko; Last updated Sep. 25, 2008; First available Jul. 6, 1989.

Tuffereau, C., et al., "Low Affinity Nerve Growth Factor Receptor (P75NTR) Can Serve as a Receptor for Rabies Virus," *The EMBO Journal* 17(24): 7250-7259 (1998).

Van der Zee, C.E.E.M., et al., "Survival of Cholinergic Forebrain Neurons in Developing $p75^{NGFR}$-Deficient Mice," *Science* 274: 1729-1732 (1996).

Wiley, R.G., et al., "Destruction of the Cholinergic Basal Forebrain Using Immunotoxin to Rat NGF Receptor: Modeling the Cholinergic Degeneration of Alzheimer's Disease," *Journal of the Neurological Sciences* 128: 157-166 (1995).

Zupan, A.A., et al., "Identification, Purification, and Characterization of Truncated Forms of the Human Nerve Growth Factor Receptor," *Journal of Biological Chemistry* 264: 11714-11720 (1989).

Partial European Search Report, EP 99 95 3434, completed Jan. 12, 2005.

International Search Report, PCT/AU 99/00860, mailed Nov. 22, 1999.

Office Action, U.S. Appl. No. 10/921,065 dated Dec. 10, 2008.

Office Action, U.S. Appl. No. 10/921,065 dated Jul. 16, 2009.

Office Action, U.S. Appl. No. 10/921,065 dated Feb. 1, 2010.

Notice of Allowance, U.S. Appl. No. 10/921,065 dated Nov. 24, 2010.

Office Action, U.S. Appl. No. 09/821,831 mailed Mar. 18, 2004.

Notice of Abandonment, U.S. Appl. No. 09/821,831 mailed Sep. 29, 2004.

\* cited by examiner

SEQUENCE LISTING

```
<160> NUMBER OF SEQ ID NOS: 74

<210> SEQ ID NO 1
<211> LENGTH: 3260
<212> TYPE: DNA
<213> ORGANISM: Rattus norvegicus
<220> FEATURE:
<221> NAME/KEY: CDS
<222> LOCATION: (115)...(1389)

<400> SEQUENCE: 1
acagctccgg cgggcagcag gcgctggagc gcatcgcagt tcagctcagc gcagcaccat         60
cggtctgcgg agcggactga gctagaagcg gagcgctgac gccggaggcg tgca atg        117
                                                                Met
                                                                 1 agg agg gca ggt gct gcc tgc agc gcc atg gac cgg ctg cgc ctg ctg        165
Arg Arg Ala Gly Ala Ala Cys Ser Ala Met Asp Arg Leu Arg Leu Leu
              5                  10                  15 ctg ctg ctg att cta ggg gtg tcc tct gga ggt gcc aag gag aca tgt        213
Leu Leu Leu Ile Leu Gly Val Ser Ser Gly Gly Ala Lys Glu Thr Cys
         20                  25                  30 tcc aca ggc ctg tac acc cac agc gga gag tgc tgc aaa gcc tgc aac        261
Ser Thr Gly Leu Tyr Thr His Ser Gly Glu Cys Cys Lys Ala Cys Asn
     35                  40                  45 ttg ggc gaa ggc gtg gcc cag ccc tgc gga gcc aac cag acc gtg tgt        309
Leu Gly Glu Gly Val Ala Gln Pro Cys Gly Ala Asn Gln Thr Val Cys
 50                  55                  60                  65
```

```
gaa ccc tgc ctg gac aat gtt aca ttc tcc gat gtg gtg agc gcc act        357
Glu Pro Cys Leu Asp Asn Val Thr Phe Ser Asp Val Val Ser Ala Thr
             70                  75                  80 gag ccg tgc aag ccg tgc acc gag tgc ctg ggc ctg cag agc atg tcc        405
Glu Pro Cys Lys Pro Cys Thr Glu Cys Leu Gly Leu Gln Ser Met Ser
         85                  90                  95 gct ccc tgt gtg gag gca gac gat gca gtg tgc aga tgt gcc tat ggc        453
Ala Pro Cys Val Glu Ala Asp Asp Ala Val Cys Arg Cys Ala Tyr Gly
100                 105                 110 tac tac cag gac gag gag act ggc cac tgt gag gct tgc agc gtg tgc        501
Tyr Tyr Gln Asp Glu Glu Thr Gly His Cys Glu Ala Cys Ser Val Cys
    115                 120                 125 gag gtg ggc tcg gga ctc gtg ttc tcc tgc cag gac aaa cag aac aca        549
Glu Val Gly Ser Gly Leu Val Phe Ser Cys Gln Asp Lys Gln Asn Thr
130                 135                 140                 145 gtg tgt gaa gag tgc cca gag ggc aca tac tca gac gaa gcc aac cac        597
Val Cys Glu Glu Cys Pro Glu Gly Thr Tyr Ser Asp Glu Ala Asn His
                150                 155                 160 gtg gac ccg tgc cta ccc tgc acg gtg tgc gag gac act gag cgc cag        645
Val Asp Pro Cys Leu Pro Cys Thr Val Cys Glu Asp Thr Glu Arg Gln
            165                 170                 175 tta cgc gag tgc acg ccc tgg gct gat gct gaa tgc gaa gag atc cct        693
Leu Arg Glu Cys Thr Pro Trp Ala Asp Ala Glu Cys Glu Glu Ile Pro
        180                 185                 190 ggt cga tgg atc cca agg tct acg ccc cga ggc tcc gac agc aca           741
Gly Arg Trp Ile Pro Arg Ser Thr Pro Pro Glu Gly Ser Asp Ser Thr
    195                 200                 205 gcg ccc agc acc cag gag cct gag gtt cct cca gag caa gac ctt gta        789
Ala Pro Ser Thr Gln Glu Pro Glu Val Pro Pro Glu Gln Asp Leu Val
210                 215                 220                 225 ccc agt aca gtg gcg gat atg gtg acc act gtg atg ggc agc tcc cag        837
Pro Ser Thr Val Ala Asp Met Val Thr Thr Val Met Gly Ser Ser Gln
                230                 235                 240 cct gta gtg acc cgc ggc acc acc gac aac ctc att cct gtc tat tgc        885
Pro Val Val Thr Arg Gly Thr Thr Asp Asn Leu Ile Pro Val Tyr Cys
            245                 250                 255 tcc atc ttg gct gct gtg gtc gtg ggc ctt gtg gcc tat att gct ttc        933
Ser Ile Leu Ala Ala Val Val Val Gly Leu Val Ala Tyr Ile Ala Phe
        260                 265                 270 aag agg tgg aac agc tgc aaa caa aat aaa caa ggc gcc aac agc cgc        981
Lys Arg Trp Asn Ser Cys Lys Gln Asn Lys Gln Gly Ala Asn Ser Arg
    275                 280                 285 ccc gtg aac cag acg ccc cca ccg gag gga gag aaa ctg cac agc gac       1029
Pro Val Asn Gln Thr Pro Pro Pro Glu Gly Glu Lys Leu His Ser Asp
290                 295                 300                 305 agt ggc atc tct gtg gac agc cag agc ctg cac gac cag cag acc cat       1077
Ser Gly Ile Ser Val Asp Ser Gln Ser Leu His Asp Gln Gln Thr His
                310                 315                 320 acg cag act gcc tca ggc cag gcc ctc aag ggt gat ggc aac ctc tac       1125
Thr Gln Thr Ala Ser Gly Gln Ala Leu Lys Gly Asp Gly Asn Leu Tyr
            325                 330                 335 agt agc ctg ccc ctg acc aag cgt gag gag gta gag aaa ctc ctc aac       1173
Ser Ser Leu Pro Leu Thr Lys Arg Glu Glu Val Glu Lys Leu Leu Asn
        340                 345                 350 ggg gat acc tgg cga cat ctg gca ggc gag ctg ggt tac cag cct gaa       1221
Gly Asp Thr Trp Arg His Leu Ala Gly Glu Leu Gly Tyr Gln Pro Glu
    355                 360                 365 cat ata gac tcc ttt acc cac gag gcc tgc cca gtg cga gcc ctg ctg       1269
His Ile Asp Ser Phe Thr His Glu Ala Cys Pro Val Arg Ala Leu Leu
370                 375                 380                 385
```

| | | |
|---|---|---|
| gcc agc tgg ggt gcc cag gac agt gca acg ctt gat gcc ctt tta gcc<br>Ala Ser Trp Gly Ala Gln Asp Ser Ala Thr Leu Asp Ala Leu Leu Ala<br>390                         395                    400 | | 1317 |
| gcc ctg cga cgc atc cag aga gct gac att gtg gag agt cta tgc agc<br>Ala Leu Arg Arg Ile Gln Arg Ala Asp Ile Val Glu Ser Leu Cys Ser<br>405                        410                    415 | | 1365 |
| gag tcc act gcc aca tcc cca gtg tgaactcaca gactgggagc ccctgtcctg<br>Glu Ser Thr Ala Thr Ser Pro Val<br>420                        425 | | 1419 |
| tcccacattc cgacgactga tgttctagcc agccccaca gagctgcccc ctctccctcg | | 1479 |
| gggatggccc aacggtcaga acggagcatc tctgtgcagg gcctctgtgt tcccactcct | | 1539 |
| gactccgttg ctgctcccga gggggcccct gcttctgacc ccctctcct cagcaagaga | | 1599 |
| gagagagagg accacccgag cctgacttgc tccatttcca tctcaggcct ttccttcctt | | 1659 |
| tctacacatt agctgtgtca gatctggggg tttgacacta ggagaaggga gcggggcac | | 1719 |
| ccctaagact caggaggtac tgaagaacca gagccatgga ctccacactg tgaaccggag | | 1779 |
| aacaaggggc ggggcattgt ggtaggctag accttcctta gcccctccct tctcccctct | | 1839 |
| ggccaaagaa gaggattacg gacctatctg agctgaaagc aggtttggaa cccagcccac | | 1899 |
| acttctctct cacacacagg atggtaaaac ccagagaaag gcagggactg acctaggcca | | 1959 |
| cccaaccaca ggaagaacaa atgaaggctg atacactccg tttctgaatg agggcgtcaa | | 2019 |
| gtgtgcttgt tgacagggat ggcgtgactt tcagggaaat atctggaagc catgtctgcc | | 2079 |
| ccgcccctcaa ccacttccag gcccctaccc aaccccttgtg cagatgaact gtttgttcaa | | 2139 |
| gggctggtcc attggtctat tctgatggag tcaagctaag ggctcaggct tatccataag | | 2199 |
| gcatttgtgg agagatgaat ctgttagtgc gctcattctt ggcataagcc tgaagccaac | | 2259 |
| acggcccta atgtcagccc tcggggtcag gaaccaagga ctcccacccc acaatccaac | | 2319 |
| actatactac attacacaca cacacacaca cacacacaca cacacacaca cacacacaca | | 2379 |
| gatatcttgc ttttctcccc atggctcttt tggggctgag actagatcct gctgggagtc | | 2439 |
| actgccagtg agagatccgg aggggacaga gctgagcttc atggggctgt cttcctcgcc | | 2499 |
| cccgggtctg gcaggccaag aatgactgca tctgagctgg tgtctgtctt ccaatggcct | | 2559 |
| gtgcgtggag gaaatgctcc cactcctccc cttcttgaag ctgcccccag aagactacag | | 2619 |
| tgcaaaagag cagactggtg tgagaacaca agaaaaagca gatgctggcc ctgcagtctg | | 2679 |
| tggcagcttt ctcctcagct tcaaggcccc tgcaaaggac ggatttcctg agcacggcca | | 2739 |
| ggaaggggca agagggttcg gttcagtggc gctttctccc ggctccttgg cctgttctgt | | 2799 |
| tttgcttgct gttggaatga gtgggcaccc cctctattta gcatgaagga gccccaggca | | 2859 |
| gggtatgcac agactgacca ccatccctcc ccacccaggg tccacccaac ccggtgaaga | | 2919 |
| gaccaggagc attgtacgca tacgcgggtg gtattttat ggaccccaat ctgcaattcc | | 2979 |
| cagacacctg ggaagtggga cattctttgt gtatttattt tcctcccag gagctgggga | | 3039 |
| gtggtggggg gctgcaggta cggtttagca tgtgtttggt tctggggtc tctccagcct | | 3099 |
| tgttttgggc caagttggaa cctctggccc tccagctggt gactatgaac tccagacccc | | 3159 |
| ttcgtgctcc ccgacgcctt cccttgcat cctgtgtaac catttcgttg ggccctccca | | 3219 |
| aaacctacac ataaaacata caggaggacc attaaattgg c | | 3260 |

<210> SEQ ID NO 2
<211> LENGTH: 425
<212> TYPE: PRT
<213> ORGANISM: Rattus norvegicus

<400> SEQUENCE: 2

```
Met Arg Arg Ala Gly Ala Ala Cys Ser Ala Met Asp Arg Leu Arg Leu
 1               5                  10                  15
Leu Leu Leu Leu Ile Leu Gly Val Ser Ser Gly Gly Ala Lys Glu Thr
            20                  25                  30
Cys Ser Thr Gly Leu Tyr Thr His Ser Gly Glu Cys Cys Lys Ala Cys
        35                  40                  45
Asn Leu Gly Glu Gly Val Ala Gln Pro Cys Gly Ala Asn Gln Thr Val
    50                  55                  60
Cys Glu Pro Cys Leu Asp Asn Val Thr Phe Ser Asp Val Val Ser Ala
65                  70                  75                  80
Thr Glu Pro Cys Lys Pro Cys Thr Glu Cys Leu Gly Leu Gln Ser Met
                85                  90                  95
Ser Ala Pro Cys Val Glu Ala Asp Asp Ala Val Cys Arg Cys Ala Tyr
            100                 105                 110
Gly Tyr Tyr Gln Asp Glu Glu Thr Gly His Cys Glu Ala Cys Ser Val
        115                 120                 125
Cys Glu Val Gly Ser Gly Leu Val Phe Ser Cys Gln Asp Lys Gln Asn
    130                 135                 140
Thr Val Cys Glu Glu Cys Pro Glu Gly Thr Tyr Ser Asp Glu Ala Asn
145                 150                 155                 160
His Val Asp Pro Cys Leu Pro Cys Thr Val Cys Glu Asp Thr Glu Arg
                165                 170                 175
Gln Leu Arg Glu Cys Thr Pro Trp Ala Asp Ala Glu Cys Glu Glu Ile
            180                 185                 190
Pro Gly Arg Trp Ile Pro Arg Ser Thr Pro Pro Glu Gly Ser Asp Ser
        195                 200                 205
Thr Ala Pro Ser Thr Gln Glu Pro Glu Val Pro Pro Glu Gln Asp Leu
    210                 215                 220
Val Pro Ser Thr Val Ala Asp Met Val Thr Thr Val Met Gly Ser Ser
225                 230                 235                 240
Gln Pro Val Val Thr Arg Gly Thr Thr Asp Asn Leu Ile Pro Val Tyr
                245                 250                 255
Cys Ser Ile Leu Ala Ala Val Val Val Gly Leu Val Ala Tyr Ile Ala
            260                 265                 270
Phe Lys Arg Trp Asn Ser Cys Lys Gln Asn Lys Gln Gly Ala Asn Ser
        275                 280                 285
Arg Pro Val Asn Gln Thr Pro Pro Glu Gly Glu Lys Leu His Ser
    290                 295                 300
Asp Ser Gly Ile Ser Val Asp Ser Gln Ser Leu His Asp Gln Gln Thr
305                 310                 315                 320
His Thr Gln Thr Ala Ser Gly Gln Ala Leu Lys Gly Asp Gly Asn Leu
                325                 330                 335
Tyr Ser Ser Leu Pro Leu Thr Lys Arg Glu Glu Val Glu Lys Leu Leu
            340                 345                 350
Asn Gly Asp Thr Trp Arg His Leu Ala Gly Glu Leu Gly Tyr Gln Pro
        355                 360                 365
Glu His Ile Asp Ser Phe Thr His Glu Ala Cys Pro Val Arg Ala Leu
    370                 375                 380
Leu Ala Ser Trp Gly Ala Gln Asp Ser Ala Thr Leu Asp Ala Leu Leu
385                 390                 395                 400
Ala Ala Leu Arg Arg Ile Gln Arg Ala Asp Ile Val Glu Ser Leu Cys
                405                 410                 415
```

```
Ser Glu Ser Thr Ala Thr Ser Pro Val
        420                 425
```

<210> SEQ ID NO 3
<211> LENGTH: 867
<212> TYPE: DNA
<213> ORGANISM: Rattus norvegicus
<220> FEATURE:
<221> NAME/KEY: CDS
<222> LOCATION: (115)...(867)

<400> SEQUENCE: 3

```
acagctccgg cgggcagcag gcgctggagc gcatcgcagt tcagctcagc gcagcaccat      60
cggtctgcgg agcggactga gctagaagcg gagcgctgac gccggaggcg tgca atg     117
                                                             Met
                                                               1 agg agg gca ggt gct gcc tgc agc gcc atg gac cgg ctg cgc ctg ctg     165
Arg Arg Ala Gly Ala Ala Cys Ser Ala Met Asp Arg Leu Arg Leu Leu
          5                  10                  15 ctg ctg ctg att cta ggg gtg tcc tct gga ggt gcc aag gag aca tgt     213
Leu Leu Leu Ile Leu Gly Val Ser Ser Gly Gly Ala Lys Glu Thr Cys
         20                  25                  30 tcc aca ggc ctg tac acc cac agc gga gag tgc tgc aaa gcc tgc aac     261
Ser Thr Gly Leu Tyr Thr His Ser Gly Glu Cys Cys Lys Ala Cys Asn
     35                  40                  45 ttg ggc gaa ggc gtg gcc cag ccc tgc gga gcc aac cag acc gtg tgt     309
Leu Gly Glu Gly Val Ala Gln Pro Cys Gly Ala Asn Gln Thr Val Cys
 50                  55                  60                  65 gaa ccc tgc ctg gac aat gtt aca ttc tcc gat gtg gtg agc gcc act     357
Glu Pro Cys Leu Asp Asn Val Thr Phe Ser Asp Val Val Ser Ala Thr
                 70                  75                  80 gag ccg tgc aag ccg tgc acc gag tgc ctg ggc ctg cag agc atg tcc     405
Glu Pro Cys Lys Pro Cys Thr Glu Cys Leu Gly Leu Gln Ser Met Ser
             85                  90                  95 gct ccc tgt gtg gag gca gac gat gca gtg tgc aga tgt gcc tat ggc     453
Ala Pro Cys Val Glu Ala Asp Asp Ala Val Cys Arg Cys Ala Tyr Gly
        100                 105                 110 tac tac cag gac gag gag act ggc cac tgt gag gct tgc agc gtg tgc     501
Tyr Tyr Gln Asp Glu Glu Thr Gly His Cys Glu Ala Cys Ser Val Cys
    115                 120                 125 gag gtg ggc tcg gga ctc gtg ttc tcc tgc cag gac aaa cag aac aca     549
Glu Val Gly Ser Gly Leu Val Phe Ser Cys Gln Asp Lys Gln Asn Thr
130                 135                 140                 145 gtg tgt gaa gag tgc cca gag ggc aca tac tca gac gaa gcc aac cac     597
Val Cys Glu Glu Cys Pro Glu Gly Thr Tyr Ser Asp Glu Ala Asn His
                150                 155                 160 gtg gac ccg tgc cta ccc tgc acg gtg tgc gag gac act gag cgc cag     645
Val Asp Pro Cys Leu Pro Cys Thr Val Cys Glu Asp Thr Glu Arg Gln
            165                 170                 175 tta cgc gag tgc acg ccc tgg gct gat gct gaa tgc gaa gag atc cct     693
Leu Arg Glu Cys Thr Pro Trp Ala Asp Ala Glu Cys Glu Glu Ile Pro
        180                 185                 190 ggt cga tgg atc cca agg tct acg ccc cga gag ggc tcc gac agc aca     741
Gly Arg Trp Ile Pro Arg Ser Thr Pro Arg Glu Gly Ser Asp Ser Thr
    195                 200                 205 gcg ccc agc acc cag gag cct gag gtt cct cca gag caa gac ctt gta     789
Ala Pro Ser Thr Gln Glu Pro Glu Val Pro Pro Glu Gln Asp Leu Val
210                 215                 220                 225 ccc agt aca gtg gcg gat atg gtg acc act gtg atg ggc agc tcc cag     837
Pro Ser Thr Val Ala Asp Met Val Thr Thr Val Met Gly Ser Ser Gln
                230                 235                 240
```

```
cct gta gtg acc cgc ggc acc acc gac aac                          867
Pro Val Val Thr Arg Gly Thr Thr Asp Asn
            245                 250
```

<210> SEQ ID NO 4
<211> LENGTH: 251
<212> TYPE: PRT
<213> ORGANISM: Rattus norvegicus

<400> SEQUENCE: 4

```
Met Arg Arg Ala Gly Ala Ala Cys Ser Ala Met Asp Arg Leu Arg Leu
  1               5                  10                  15

Leu Leu Leu Leu Ile Leu Gly Val Ser Ser Gly Ala Lys Glu Thr
                 20                  25                  30

Cys Ser Thr Gly Leu Tyr Thr His Ser Gly Glu Cys Cys Lys Ala Cys
             35                  40                  45

Asn Leu Gly Glu Gly Val Ala Gln Pro Cys Gly Ala Asn Gln Thr Val
 50                  55                  60

Cys Glu Pro Cys Leu Asp Asn Val Thr Phe Ser Asp Val Val Ser Ala
 65                  70                  75                  80

Thr Glu Pro Cys Lys Pro Cys Thr Glu Cys Leu Gly Leu Gln Ser Met
                 85                  90                  95

Ser Ala Pro Cys Val Glu Ala Asp Ala Val Cys Arg Cys Ala Tyr
                100                 105                 110

Gly Tyr Tyr Gln Asp Glu Glu Thr Gly His Cys Glu Ala Cys Ser Val
             115                 120                 125

Cys Glu Val Gly Ser Gly Leu Val Phe Ser Cys Gln Asp Lys Gln Asn
130                 135                 140

Thr Val Cys Glu Glu Cys Pro Glu Gly Thr Tyr Ser Asp Glu Ala Asn
145                 150                 155                 160

His Val Asp Pro Cys Leu Pro Cys Thr Val Cys Glu Asp Thr Glu Arg
                165                 170                 175

Gln Leu Arg Glu Cys Thr Pro Trp Ala Asp Ala Glu Cys Glu Glu Ile
            180                 185                 190

Pro Gly Arg Trp Ile Pro Arg Ser Thr Pro Glu Gly Ser Asp Ser
            195                 200                 205

Thr Ala Pro Ser Thr Gln Glu Pro Glu Val Pro Pro Glu Gln Asp Leu
210                 215                 220

Val Pro Ser Thr Val Ala Asp Met Val Thr Thr Val Met Gly Ser Ser
225                 230                 235                 240

Gln Pro Val Val Thr Arg Gly Thr Thr Asp Asn
                245                 250
```

<210> SEQ ID NO 5
<211> LENGTH: 66
<212> TYPE: DNA
<213> ORGANISM: Rattus norvegicus
<220> FEATURE:
<221> NAME/KEY: CDS
<222> LOCATION: (1)...(66)

<400> SEQUENCE: 5

```
ctc att cct gtc tat tgc tcc atc ttg gct gct gtg gtc gtg ggc ctt   48
Leu Ile Pro Val Tyr Cys Ser Ile Leu Ala Ala Val Val Val Gly Leu
  1               5                  10                  15 gtg gcc tat att gct ttc                                           66
Val Ala Tyr Ile Ala Phe
                 20
```

<210> SEQ ID NO 6
<211> LENGTH: 22
<212> TYPE: PRT
<213> ORGANISM: Rattus norvegicus

<400> SEQUENCE: 6

Leu Ile Pro Val Tyr Cys Ser Ile Leu Ala Ala Val Val Gly Leu
1               5                   10                  15

Val Ala Tyr Ile Ala Phe
            20

<210> SEQ ID NO 7
<211> LENGTH: 105
<212> TYPE: DNA
<213> ORGANISM: Rattus norvegicus

<400> SEQUENCE: 7
aagaggtgga acagctgcaa acaaaataaa caaggcgcca acagccgccc cgtgaaccag      60
acgcccccac cggagggaga gaaactgcac agcgacagtg gcatc                    105

<210> SEQ ID NO 8
<211> LENGTH: 35
<212> TYPE: PRT
<213> ORGANISM: Rattus norvegicus

<400> SEQUENCE: 8

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu His Ser Asp
            20                  25                  30

Ser Gly Ile
        35

<210> SEQ ID NO 9
<211> LENGTH: 2222
<212> TYPE: DNA
<213> ORGANISM: Rattus norvegicus
<220> FEATURE:
<221> NAME/KEY: CDS
<222> LOCATION: (1)...(351)

<400> SEQUENCE: 9

| tct | gtg | gac | agc | cag | agc | ctg | cac | gac | cag | cag | acc | cat | acg | cag | act |  48 |
|-----|-----|-----|-----|-----|-----|-----|-----|-----|-----|-----|-----|-----|-----|-----|-----|-----|
| Ser | Val | Asp | Ser | Gln | Ser | Leu | His | Asp | Gln | Gln | Thr | His | Thr | Gln | Thr |     |
| 1   |     |     |     | 5   |     |     |     |     | 10  |     |     |     |     | 15  |     |     |

| gcc | tca | ggc | cag | gcc | ctc | aag | ggt | gat | ggc | aac | ctc | tac | agt | agc | ctg |  96 |
| Ala | Ser | Gly | Gln | Ala | Leu | Lys | Gly | Asp | Gly | Asn | Leu | Tyr | Ser | Ser | Leu |     |
|     |     |     |     | 20  |     |     |     |     | 25  |     |     |     |     | 30  |     |     |

| ccc | ctg | acc | aag | cgt | gag | gag | gta | gag | aaa | ctg | ctc | aac | ggg | gat | acc | 144 |
| Pro | Leu | Thr | Lys | Arg | Glu | Glu | Val | Glu | Lys | Leu | Leu | Asn | Gly | Asp | Thr |     |
|     |     | 35  |     |     |     |     | 40  |     |     |     |     | 45  |     |     |     |     |

| tgg | cga | cat | ctg | gca | ggc | gag | ctg | ggt | tac | cag | cct | gaa | cat | ata | gac | 192 |
| Trp | Arg | His | Leu | Ala | Gly | Glu | Leu | Gly | Tyr | Gln | Pro | Glu | His | Ile | Asp |     |
|     | 50  |     |     |     |     | 55  |     |     |     |     | 60  |     |     |     |     |     |

| tcc | ttt | acc | cac | gag | gcc | tgc | cca | gtg | cga | gcc | ctg | ctg | gcc | agc | tgg | 240 |
| Ser | Phe | Thr | His | Glu | Ala | Cys | Pro | Val | Arg | Ala | Leu | Leu | Ala | Ser | Trp |     |
| 65  |     |     |     |     | 70  |     |     |     |     | 75  |     |     |     |     | 80  |     |

| ggt | gcc | cag | gac | agt | gca | acg | ctt | gat | gcc | ctt | tta | gcc | gcc | ctg | cga | 288 |
| Gly | Ala | Gln | Asp | Ser | Ala | Thr | Leu | Asp | Ala | Leu | Leu | Ala | Ala | Leu | Arg |     |
|     |     |     |     | 85  |     |     |     |     | 90  |     |     |     |     | 95  |     |     |

| cgc | atc | cag | aga | gct | gac | att | gtg | gag | agt | cta | tgc | agc | gag | tcc | act | 336 |
| Arg | Ile | Gln | Arg | Ala | Asp | Ile | Val | Glu | Ser | Leu | Cys | Ser | Glu | Ser | Thr |     |

```
                   100             105             110
gcc aca tcc cca gtg tgaactcaca gactgggagc ccctgtcctg tcccacattc    391
Ala Thr Ser Pro Val
        115 cgacgactga tgttctagcc agccccaca gagctgcccc ctctccctcg gggatggccc    451
aacggtcaga acggagcatc tctgtgcagg gcctctgtgt cccactcct gactccgttg    511
ctgctcccga gggggcctt gcttctgacc accctctcct cagcaagaga gagagagagg    571
accacccgag cctgacttgc tccatttcca tctcaggcct ttccttcctt tctacacatt    631
agctgtgtca gatctggggg tttgacacta ggagaaggga gcggggcac ccctaagact    691
caggaggtac tgaagaacca gagccatgga ctccacactg tgaaccggag aacaaggggc    751
ggggcattgt ggtaggctag accttcctta gcccctccct tctcccctct ggccaaagaa    811
gaggattacg gacctatctg agctgaaagc aggtttggaa cccagcccac acttctctct    871
cacacacagg atggtaaaac ccagagaaag gcagggactg acctaggcca cccaaccaca    931
ggaagaacaa atgaaggctg atacactccg tttctgaatg agggcgtcaa gtgtgcttgt    991
tgacagggat ggcgtgactt tcagggaaat atctggaagc catgtctgcc ccgccctcaa   1051
ccacttccag gcccctaccc aacccttgtg cagatgaact gtttgttcaa gggctggtcc   1111
attggtctat tctgatggag tcaagctaag ggctcaggct tatccataag gcatttgtgg   1171
agagatgaat ctgttagtgc gctcattctt ggcataagcc tgaagccaac acggcccta   1231
atgtcagccc tcggggtcag gaaccaagga ctcccacccc acaatccaac actatactac   1291
attacacaca cacacacaca cacacacaca cacacacaca cacacacaca gatatcttgc   1351
ttttctcccc atggctcttt tggggctgag actagatcct gctggagtc actgccagtg   1411
agagatccgg aggggacaga gctgagcttc atggggctgt cttcctcgcc cccgggtctg   1471
gcaggccaag aatgactgca tctgagctgg tgtctgtctt ccaatggcct gtgcgtggag   1531
gaaatgctcc cactcctccc cttcttgaag ctgcccccag aagactacag tgcaaaagag   1591
cagactggtg tgagaacaca agaaaaagca gatgctggcc ctgcagtctg tggcagcttt   1651
ctcctcagct tcaaggcccc tgcaaaggac ggatttcctg agcacggcca ggaagggca   1711
agagggttcg gttcagtggc gctttctccc ggctccttgg cctgttctgt tttgcttgct   1771
gttggaatga gtgggcaccc cctctattta gcatgaagga gccccaggca gggtatgcac   1831
agactgacca ccatccctcc ccacccaggg tccacccaac ccggtgaaga gaccaggagc   1891
attgtacgca tacgcgggtg gtattttat ggaccccaat ctgcaattcc cagacacctg   1951
ggaagtggga cattctttgt gtatttattt tcctccccag gagctgggga gtggtggggg   2011
gctgcaggta cggtttagca tgtgtttggt tctgggggtc tctccagcct tgttttgggc   2071
caagttggaa cctctggccc tccagctggt gactatgaac tccagacccc ttcgtgctcc   2131
ccgacgcctt ccccttgcat cctgtgtaac catttcgttg ggccctccca aaacctacac   2191
ataaaacata caggaggacc attaaattgg c                                 2222
```

<210> SEQ ID NO 10
<211> LENGTH: 117
<212> TYPE: PRT
<213> ORGANISM: Rattus norvegicus
<400> SEQUENCE: 10

```
Ser Val Asp Ser Gln Ser Leu His Asp Gln Gln Thr His Thr Gln Thr
1               5                   10                  15

Ala Ser Gly Gln Ala Leu Lys Gly Asp Gly Asn Leu Tyr Ser Ser Leu
```

-continued

```
                20                  25                  30
Pro Leu Thr Lys Arg Glu Glu Val Glu Lys Leu Leu Asn Gly Asp Thr
        35                  40                  45

Trp Arg His Leu Ala Gly Glu Leu Gly Tyr Gln Pro Glu His Ile Asp
 50                  55                  60

Ser Phe Thr His Glu Ala Cys Pro Val Arg Ala Leu Leu Ala Ser Trp
 65                  70                  75                  80

Gly Ala Gln Asp Ser Ala Thr Leu Asp Ala Leu Leu Ala Leu Arg
                85                  90                  95

Arg Ile Gln Arg Ala Asp Ile Val Glu Ser Leu Cys Ser Glu Ser Thr
                100                 105                 110

Ala Thr Ser Pro Val
        115

<210> SEQ ID NO 11
<211> LENGTH: 87
<212> TYPE: DNA
<213> ORGANISM: Rattus norvegicus
<220> FEATURE:
<221> NAME/KEY: CDS
<222> LOCATION: (1)...(87)

<400> SEQUENCE: 11 aag agg tgg aac agc tgc aaa caa aat aaa caa ggc gcc aac agc cgc      48
Lys Arg Trp Asn Ser Cys Lys Gln Asn Lys Gln Gly Ala Asn Ser Arg
 1               5                  10                  15 ccc gtg aac cag acg ccc cca ccg gag gga gag aaa ctg               87
Pro Val Asn Gln Thr Pro Pro Pro Glu Gly Glu Lys Leu
                20                  25

<210> SEQ ID NO 12
<211> LENGTH: 29
<212> TYPE: PRT
<213> ORGANISM: Rattus norvegicus

<400> SEQUENCE: 12

Lys Arg Trp Asn Ser Cys Lys Gln Asn Lys Gln Gly Ala Asn Ser Arg
 1               5                  10                  15

Pro Val Asn Gln Thr Pro Pro Pro Glu Gly Glu Lys Leu
                20                  25

<210> SEQ ID NO 13
<211> LENGTH: 34
<212> TYPE: PRT
<213> ORGANISM: Rattus norvegicus

<400> SEQUENCE: 13

Lys Arg Trp Asn Ser Cys Lys Gln Asn Lys Gln Gly Ala Asn Ser Arg
 1               5                  10                  15

Pro Val Asn Gln Thr Pro Pro Pro Glu Gly Glu Lys Leu His Ser Asp
                20                  25                  30

Ser Gly

<210> SEQ ID NO 14
<211> LENGTH: 33
<212> TYPE: PRT
<213> ORGANISM: Rattus norvegicus

<400> SEQUENCE: 14

Lys Arg Trp Asn Ser Cys Lys Gln Asn Lys Gln Gly Ala Asn Ser Arg
 1               5                  10                  15
```

-continued

Pro Val Asn Gln Thr Pro Pro Glu Gly Glu Lys Leu His Ser Asp
            20                  25                  30

Ser

<210> SEQ ID NO 15
<211> LENGTH: 32
<212> TYPE: PRT
<213> ORGANISM: Rattus norvegicus

<400> SEQUENCE: 15

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu His Ser Asp
            20                  25                  30

<210> SEQ ID NO 16
<211> LENGTH: 31
<212> TYPE: PRT
<213> ORGANISM: Rattus norvegicus

<400> SEQUENCE: 16

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu His Ser
            20                  25                  30

<210> SEQ ID NO 17
<211> LENGTH: 30
<212> TYPE: PRT
<213> ORGANISM: Rattus norvegicus

<400> SEQUENCE: 17

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu His
            20                  25                  30

<210> SEQ ID NO 18
<211> LENGTH: 29
<212> TYPE: PRT
<213> ORGANISM: Rattus norvegicus

<400> SEQUENCE: 18

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys Leu
            20                  25

<210> SEQ ID NO 19
<211> LENGTH: 28
<212> TYPE: PRT
<213> ORGANISM: Rattus norvegicus

<400> SEQUENCE: 19

Lys Arg Trp Asn Ser Cys Lys Gln Asn Lys Gln Gly Ala Asn Ser Arg
1               5                   10                  15

Pro Val Asn Gln Thr Pro Pro Glu Gly Glu Lys
            20                  25

<210> SEQ ID NO 20
<211> LENGTH: 27
<212> TYPE: PRT
<213> ORGANISM: Rattus norvegicus -continued

<400> SEQUENCE: 20

Lys Arg Trp Asn Ser Cys Lys Gln Asn Lys Gln Gly Ala Asn Ser Arg
1               5                   10                  15

Pro Val Asn Gln Thr Pro Pro Pro Glu Gly Glu
            20                  25

<210> SEQ ID NO 21
<211> LENGTH: 26
<212> TYPE: PRT
<213> ORGANISM: Rattus norvegicus

<400> SEQUENCE: 21

Lys Arg Trp Asn Ser Cys Lys Gln Asn Lys Gln Gly Ala Asn Ser Arg
1               5                   10                  15

Pro Val Asn Gln Thr Pro Pro Pro Glu Gly
            20                  25

<210> SEQ ID NO 22
<211> LENGTH: 25
<212> TYPE: PRT
<213> ORGANISM: Rattus norvegicus

<400> SEQUENCE: 22

Lys Arg Trp Asn Ser Cys Lys Gln Asn Lys Gln Gly Ala Asn Ser Arg
1               5                   10                  15

Pro Val Asn Gln Thr Pro Pro Pro Glu
            20                  25

<210> SEQ ID NO 23
<211> LENGTH: 24
<212> TYPE: PRT
<213> ORGANISM: Rattus norvegicus

<400> SEQUENCE: 23

Lys Arg Trp Asn Ser Cys Lys Gln Asn Lys Gln Gly Ala Asn Ser Arg
1               5                   10                  15

Pro Val Asn Gln Thr Pro Pro Pro
            20

<210> SEQ ID NO 24
<211> LENGTH: 23
<212> TYPE: PRT
<213> ORGANISM: Rattus norvegicus

<400> SEQUENCE: 24

Lys Arg Trp Asn Ser Cys Lys Gln Asn Lys Gln Gly Ala Asn Ser Arg
1               5                   10                  15

Pro Val Asn Gln Thr Pro Pro
            20

<210> SEQ ID NO 25
<211> LENGTH: 22
<212> TYPE: PRT
<213> ORGANISM: Rattus norvegicus

<400> SEQUENCE: 25

Lys Arg Trp Asn Ser Cys Lys Gln Asn Lys Gln Gly Ala Asn Ser Arg
1               5                   10                  15

Pro Val Asn Gln Thr Pro
            20

```
<210> SEQ ID NO 26
<211> LENGTH: 21
<212> TYPE: PRT
<213> ORGANISM: Rattus norvegicus

<400> SEQUENCE: 26

Lys Arg Trp Asn Ser Cys Lys Gln Asn Lys Gln Gly Ala Asn Ser Arg
 1               5                  10                  15

Pro Val Asn Gln Thr
            20

<210> SEQ ID NO 27
<211> LENGTH: 20
<212> TYPE: PRT
<213> ORGANISM: Rattus norvegicus

<400> SEQUENCE: 27

Lys Arg Trp Asn Ser Cys Lys Gln Asn Lys Gln Gly Ala Asn Ser Arg
 1               5                  10                  15

Pro Val Asn Gln
            20

<210> SEQ ID NO 28
<211> LENGTH: 19
<212> TYPE: PRT
<213> ORGANISM: Rattus norvegicus

<400> SEQUENCE: 28

Lys Arg Trp Asn Ser Cys Lys Gln Asn Lys Gln Gly Ala Asn Ser Arg
 1               5                  10                  15

Pro Val Asn

<210> SEQ ID NO 29
<211> LENGTH: 18
<212> TYPE: PRT
<213> ORGANISM: Rattus norvegicus

<400> SEQUENCE: 29

Lys Arg Trp Asn Ser Cys Lys Gln Asn Lys Gln Gly Ala Asn Ser Arg
 1               5                  10                  15

Pro Val

<210> SEQ ID NO 30
<211> LENGTH: 17
<212> TYPE: PRT
<213> ORGANISM: Rattus norvegicus

<400> SEQUENCE: 30

Lys Arg Trp Asn Ser Cys Lys Gln Asn Lys Gln Gly Ala Asn Ser Arg
 1               5                  10                  15

Pro

<210> SEQ ID NO 31
<211> LENGTH: 16
<212> TYPE: PRT
<213> ORGANISM: Rattus norvegicus

<400> SEQUENCE: 31

Lys Arg Trp Asn Ser Cys Lys Gln Asn Lys Gln Gly Ala Asn Ser Arg
 1               5                  10                  15

<210> SEQ ID NO 32
<211> LENGTH: 15
```

<212> TYPE: PRT
<213> ORGANISM: Rattus norvegicus

<400> SEQUENCE: 32

Lys Arg Trp Asn Ser Cys Lys Gln Asn Lys Gln Gly Ala Asn Ser
1               5                   10                  15

<210> SEQ ID NO 33
<211> LENGTH: 14
<212> TYPE: PRT
<213> ORGANISM: Rattus norvegicus

<400> SEQUENCE: 33

Lys Arg Trp Asn Ser Cys Lys Gln Asn Lys Gln Gly Ala Asn
1               5                   10

<210> SEQ ID NO 34
<211> LENGTH: 13
<212> TYPE: PRT
<213> ORGANISM: Rattus norvegicus

<400> SEQUENCE: 34

Lys Arg Trp Asn Ser Cys Lys Gln Asn Lys Gln Gly Ala
1               5                   10

<210> SEQ ID NO 35
<211> LENGTH: 12
<212> TYPE: PRT
<213> ORGANISM: Rattus norvegicus

<400> SEQUENCE: 35

Lys Arg Trp Asn Ser Cys Lys Gln Asn Lys Gln Gly
1               5                   10

<210> SEQ ID NO 36
<211> LENGTH: 11
<212> TYPE: PRT
<213> ORGANISM: Rattus norvegicus

<400> SEQUENCE: 36

Lys Arg Trp Asn Ser Cys Lys Gln Asn Lys Gln
1               5                   10

<210> SEQ ID NO 37
<211> LENGTH: 10
<212> TYPE: PRT
<213> ORGANISM: Rattus norvegicus

<400> SEQUENCE: 37

Lys Arg Trp Asn Ser Cys Lys Gln Asn Lys
1               5                   10

<210> SEQ ID NO 38
<211> LENGTH: 9
<212> TYPE: PRT
<213> ORGANISM: Rattus norvegicus

<400> SEQUENCE: 38

Lys Arg Trp Asn Ser Cys Lys Gln Asn
1               5

<210> SEQ ID NO 39
<211> LENGTH: 8
<212> TYPE: PRT
<213> ORGANISM: Rattus norvegicus -continued

```
<400> SEQUENCE: 39

Lys Arg Trp Asn Ser Cys Lys Gln
 1               5

<210> SEQ ID NO 40
<211> LENGTH: 7
<212> TYPE: PRT
<213> ORGANISM: Rattus norvegicus

<400> SEQUENCE: 40

Lys Arg Trp Asn Ser Cys Lys
 1               5

<210> SEQ ID NO 41
<211> LENGTH: 6
<212> TYPE: PRT
<213> ORGANISM: Rattus norvegicus

<400> SEQUENCE: 41

Lys Arg Trp Asn Ser Cys
 1               5

<210> SEQ ID NO 42
<211> LENGTH: 5
<212> TYPE: PRT
<213> ORGANISM: Rattus norvegicus

<400> SEQUENCE: 42

Lys Arg Trp Asn Ser
 1               5

<210> SEQ ID NO 43
<211> LENGTH: 4
<212> TYPE: PRT
<213> ORGANISM: Rattus norvegicus

<400> SEQUENCE: 43

Lys Arg Trp Asn
 1

<210> SEQ ID NO 44
<211> LENGTH: 34
<212> TYPE: PRT
<213> ORGANISM: Rattus norvegicus

<400> SEQUENCE: 44

Arg Trp Asn Ser Cys Lys Gln Asn Lys Gln Gly Ala Asn Ser Arg Pro
 1               5                  10                  15

Val Asn Gln Thr Pro Pro Glu Gly Glu Lys Leu His Ser Asp Ser
             20                  25                  30

Gly Ile

<210> SEQ ID NO 45
<211> LENGTH: 33
<212> TYPE: PRT
<213> ORGANISM: Rattus norvegicus

<400> SEQUENCE: 45

Trp Asn Ser Cys Lys Gln Asn Lys Gln Gly Ala Asn Ser Arg Pro Val
 1               5                  10                  15

Asn Gln Thr Pro Pro Glu Gly Glu Lys Leu His Ser Asp Ser Gly
             20                  25                  30

Ile
```

-continued

<210> SEQ ID NO 46
<211> LENGTH: 32
<212> TYPE: PRT
<213> ORGANISM: Rattus norvegicus

<400> SEQUENCE: 46

Asn Ser Cys Lys Gln Asn Lys Gln Gly Ala Asn Ser Arg Pro Val Asn
1               5                   10                  15

Gln Thr Pro Pro Pro Glu Gly Glu Lys Leu His Ser Asp Ser Gly Ile
            20                  25                  30

<210> SEQ ID NO 47
<211> LENGTH: 31
<212> TYPE: PRT
<213> ORGANISM: Rattus norvegicus

<400> SEQUENCE: 47

Ser Cys Lys Gln Asn Lys Gln Gly Ala Asn Ser Arg Pro Val Asn Gln
1               5                   10                  15

Thr Pro Pro Pro Glu Gly Glu Lys Leu His Ser Asp Ser Gly Ile
            20                  25                  30

<210> SEQ ID NO 48
<211> LENGTH: 30
<212> TYPE: PRT
<213> ORGANISM: Rattus norvegicus

<400> SEQUENCE: 48

Cys Lys Gln Asn Lys Gln Gly Ala Asn Ser Arg Pro Val Asn Gln Thr
1               5                   10                  15

Pro Pro Pro Glu Gly Glu Lys Leu His Ser Asp Ser Gly Ile
            20                  25                  30

<210> SEQ ID NO 49
<211> LENGTH: 29
<212> TYPE: PRT
<213> ORGANISM: Rattus norvegicus

<400> SEQUENCE: 49

Lys Gln Asn Lys Gln Gly Ala Asn Ser Arg Pro Val Asn Gln Thr Pro
1               5                   10                  15

Pro Pro Glu Gly Glu Lys Leu His Ser Asp Ser Gly Ile
            20                  25

<210> SEQ ID NO 50
<211> LENGTH: 28
<212> TYPE: PRT
<213> ORGANISM: Rattus norvegicus

<400> SEQUENCE: 50

Gln Asn Lys Gln Gly Ala Asn Ser Arg Pro Val Asn Gln Thr Pro Pro
1               5                   10                  15

Pro Glu Gly Glu Lys Leu His Ser Asp Ser Gly Ile
            20                  25

<210> SEQ ID NO 51
<211> LENGTH: 27
<212> TYPE: PRT
<213> ORGANISM: Rattus norvegicus

<400> SEQUENCE: 51

Asn Lys Gln Gly Ala Asn Ser Arg Pro Val Asn Gln Thr Pro Pro Pro

```
                1               5                  10                  15

Glu Gly Glu Lys Leu His Ser Asp Ser Gly Ile
            20                  25

<210> SEQ ID NO 52
<211> LENGTH: 26
<212> TYPE: PRT
<213> ORGANISM: Rattus norvegicus

<400> SEQUENCE: 52

Lys Gln Gly Ala Asn Ser Arg Pro Val Asn Gln Thr Pro Pro Glu
 1               5                  10                  15

Gly Glu Lys Leu His Ser Asp Ser Gly Ile
            20                  25

<210> SEQ ID NO 53
<211> LENGTH: 25
<212> TYPE: PRT
<213> ORGANISM: Rattus norvegicus

<400> SEQUENCE: 53

Gln Gly Ala Asn Ser Arg Pro Val Asn Gln Thr Pro Pro Glu Gly
 1               5                  10                  15

Glu Lys Leu His Ser Asp Ser Gly Ile
            20                  25

<210> SEQ ID NO 54
<211> LENGTH: 24
<212> TYPE: PRT
<213> ORGANISM: Rattus norvegicus

<400> SEQUENCE: 54

Gly Ala Asn Ser Arg Pro Val Asn Gln Thr Pro Pro Glu Gly Glu
 1               5                  10                  15

Lys Leu His Ser Asp Ser Gly Ile
            20

<210> SEQ ID NO 55
<211> LENGTH: 23
<212> TYPE: PRT
<213> ORGANISM: Rattus norvegicus

<400> SEQUENCE: 55

Ala Asn Ser Arg Pro Val Asn Gln Thr Pro Pro Glu Gly Glu Lys
 1               5                  10                  15

Leu His Ser Asp Ser Gly Ile
            20

<210> SEQ ID NO 56
<211> LENGTH: 22
<212> TYPE: PRT
<213> ORGANISM: Rattus norvegicus

<400> SEQUENCE: 56

Asn Ser Arg Pro Val Asn Gln Thr Pro Pro Glu Gly Glu Lys Leu
 1               5                  10                  15

His Ser Asp Ser Gly Ile
            20

<210> SEQ ID NO 57
<211> LENGTH: 21
<212> TYPE: PRT
<213> ORGANISM: Rattus norvegicus
```

<400> SEQUENCE: 57

Ser Arg Pro Val Asn Gln Thr Pro Pro Glu Gly Glu Lys Leu His
1               5                   10                  15

Ser Asp Ser Gly Ile
            20

<210> SEQ ID NO 58
<211> LENGTH: 20
<212> TYPE: PRT
<213> ORGANISM: Rattus norvegicus

<400> SEQUENCE: 58

Arg Pro Val Asn Gln Thr Pro Pro Glu Gly Glu Lys Leu His Ser
1               5                   10                  15

Asp Ser Gly Ile
            20

<210> SEQ ID NO 59
<211> LENGTH: 19
<212> TYPE: PRT
<213> ORGANISM: Rattus norvegicus

<400> SEQUENCE: 59

Pro Val Asn Gln Thr Pro Pro Glu Gly Glu Lys Leu His Ser Asp
1               5                   10                  15

Ser Gly Ile

<210> SEQ ID NO 60
<211> LENGTH: 18
<212> TYPE: PRT
<213> ORGANISM: Rattus norvegicus

<400> SEQUENCE: 60

Val Asn Gln Thr Pro Pro Glu Gly Glu Lys Leu His Ser Asp Ser
1               5                   10                  15

Gly Ile

<210> SEQ ID NO 61
<211> LENGTH: 17
<212> TYPE: PRT
<213> ORGANISM: Rattus norvegicus

<400> SEQUENCE: 61

Asn Gln Thr Pro Pro Glu Gly Glu Lys Leu His Ser Asp Ser Gly
1               5                   10                  15

Ile

<210> SEQ ID NO 62
<211> LENGTH: 16
<212> TYPE: PRT
<213> ORGANISM: Rattus norvegicus

<400> SEQUENCE: 62

Gln Thr Pro Pro Glu Gly Glu Lys Leu His Ser Asp Ser Gly Ile
1               5                   10                  15

<210> SEQ ID NO 63
<211> LENGTH: 15
<212> TYPE: PRT
<213> ORGANISM: Rattus norvegicus

<400> SEQUENCE: 63

```
Thr Pro Pro Pro Glu Gly Glu Lys Leu His Ser Asp Ser Gly Ile
1               5                   10                  15
```

<210> SEQ ID NO 64
<211> LENGTH: 14
<212> TYPE: PRT
<213> ORGANISM: Rattus norvegicus

<400> SEQUENCE: 64

```
Pro Pro Pro Glu Gly Glu Lys Leu His Ser Asp Ser Gly Ile
1               5                   10
```

<210> SEQ ID NO 65
<211> LENGTH: 13
<212> TYPE: PRT
<213> ORGANISM: Rattus norvegicus

<400> SEQUENCE: 65

```
Pro Pro Glu Gly Glu Lys Leu His Ser Asp Ser Gly Ile
1               5                   10
```

<210> SEQ ID NO 66
<211> LENGTH: 12
<212> TYPE: PRT
<213> ORGANISM: Rattus norvegicus

<400> SEQUENCE: 66

```
Pro Glu Gly Glu Lys Leu His Ser Asp Ser Gly Ile
1               5                   10
```

<210> SEQ ID NO 67
<211> LENGTH: 11
<212> TYPE: PRT
<213> ORGANISM: Rattus norvegicus

<400> SEQUENCE: 67

```
Glu Gly Glu Lys Leu His Ser Asp Ser Gly Ile
1               5                   10
```

<210> SEQ ID NO 68
<211> LENGTH: 10
<212> TYPE: PRT
<213> ORGANISM: Rattus norvegicus

<400> SEQUENCE: 68

```
Gly Glu Lys Leu His Ser Asp Ser Gly Ile
1               5                   10
```

<210> SEQ ID NO 69
<211> LENGTH: 9
<212> TYPE: PRT
<213> ORGANISM: Rattus norvegicus

<400> SEQUENCE: 69

```
Glu Lys Leu His Ser Asp Ser Gly Ile
1               5
```

<210> SEQ ID NO 70
<211> LENGTH: 8
<212> TYPE: PRT
<213> ORGANISM: Rattus norvegicus

<400> SEQUENCE: 70

```
Lys Leu His Ser Asp Ser Gly Ile
1               5
```

```
<210> SEQ ID NO 71
<211> LENGTH: 7
<212> TYPE: PRT
<213> ORGANISM: Rattus norvegicus

<400> SEQUENCE: 71

Leu His Ser Asp Ser Gly Ile
 1               5

<210> SEQ ID NO 72
<211> LENGTH: 6
<212> TYPE: PRT
<213> ORGANISM: Rattus norvegicus

<400> SEQUENCE: 72

His Ser Asp Ser Gly Ile
 1               5

<210> SEQ ID NO 73
<211> LENGTH: 5
<212> TYPE: PRT
<213> ORGANISM: Rattus norvegicus

<400> SEQUENCE: 73

Ser Asp Ser Gly Ile
 1               5

<210> SEQ ID NO 74
<211> LENGTH: 4
<212> TYPE: PRT
<213> ORGANISM: Rattus norvegicus

<400> SEQUENCE: 74

Asp Ser Gly Ile
 1
```

US 8,299,027 B2

METHOD OF MODULATING CELL SURVIVAL AND REAGENTS USEFUL FOR SAME

RELATED APPLICATIONS

This application is a Divisional of U.S. application Ser. No. 10/921,065, filed on Aug. 18, 2004 now U.S. Pat. No. 7,919,471, which is a Continuation of U.S. application Ser. No. 09/821,831, filed on Mar. 30, 2001, now abandoned which is a Continuation of International Application No. PCT/AU99/00860, filed on Oct. 5, 1999, which claims the benefit of Australian Provisional Patent Application No. PQ 0701, filed on Jun. 1, 1999; Australian Provisional Patent Application No. PP6351, filed on Oct. 7, 1998; and Australian Provisional Patent Application No. PP6353, filed on Oct. 6, 1998. The entire teachings of the above applications are incorporated herein by reference.

FIELD OF THE INVENTION

The present invention relates generally to a method for modulating cell survival. Modulation of cell survival includes inducing, enhancing or otherwise promoting cell survival such as the survival of neural cells as well as facilitating cell death such as the death of targeted cancer cells. The modulation of cell survival is mediated by a region identified on the p75 neurotrophin receptor ($p75^{NTR}$)) required for death signalling. The present invention further provides genetic molecules which encode the death signalling region of $p75^{NTR}$ which are useful in antagonising death signal function as well as promoting cell death when expressed in targeted cells. The present invention also contemplates recombinant peptides, polypeptides and proteins as well as chemical equivalents, derivatives and homologues thereof which comprise the death signalling portion of $p75^{NTR}$. Particularly useful molecules of the present invention comprise peptides corresponding to soluble forms of the death signalling portion of $p75^{NTR}$. These molecules antagonise $p75^{NTR}$-mediated cell death.

BACKGROUND OF THE INVENTION

Bibliographic details of the publications-numerically referred to in this specification are collected at the end of the description.

The subject specification contains nucleotide and amino acid sequence information prepared using the program FastSeq Version 4.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences which are defined in the Sequence Listing by the information provided in numeric indicator field <400> followed by the sequence identifier (eg. <400>1, <400>2, etc), are referred to in the specification as ("SEQ ID NO:1", SEQ ID NO:2, etc).

The increasing sophistication of recombinant DNA technology is greatly facilitating research and development in the medical and allied health fields. This is particularly the case in the development of recombinant cytokines and growth factors for use in the treatment of diabetes, acquired immunodeficiency syndrome (AIDS) and a number of cancers.

However, despite this developing knowledge of cytokine and growth factor effector molecules, their full exploitation requires an understanding of the corresponding cellular receptors and the complex biochemical and physiological signalling pathways initiated following interaction with ligands or following other stimulation such as disease, receptor aggregation or trauma.

A number of soluble trophic factors have been shown to exhibit an effect on neural survival in vivo. Many of these factors act directly on the developing neuron within, for example, the dorsal root ganglia (DRG). One factor of particular importance is nerve growth factor (NGF) [1]. The p75 neurotrophin receptor (hereinafter referred to as "$p75^{NTR}$"), which is capable of associating with trk growth factor receptors, facilitates high affinity NGF binding and survival signalling. Although NGF has been proposed as a potential therapeutic molecule to promote survival of neurons, NGF is a multifunctional molecule and its pleiotrophy may adversely affect a range of non-neural cells.

$p75^{NTR}$ is also multifunctional. It has now been shown that $p75^{NTR}$ is capable of acting as a death receptor. Elevated $p75^{NTR}$ expression results in increased cell death in vitro and in vivo [2-4]. Furthermore, down-regulation of $p75^{NTR}$ prevents neural death after growth-factor withdrawal or axotomy [5, 6]. Consistent with the dual functions of $p75^{NTR}$, mice with deleted $p75^{NTR}$ genes have a dramatic reduction of NGF dependent neurons, such as dorsal root ganglia, but increased numbers of other neuron populations (sympathetic and basal forebrain neurons) suggesting lack of naturally occurring cell death [7, 8]. $p75^{NTR}$ is also implicated in mediating death of neural, oligodendrocytes and Schwann cells [8, 9].

$p75^{NTR}$ is a member of the tumor necrosis factor (TNF) receptor/Fas superfamily, showing homology not only to the extracellular ligand binding domain but also to a cytoplasmic motif known as the "death domain", so termed because of the cytotoxic actions of proteins containing the domain [9].

There is an accumulating body of evidence which suggests that $p75^{NTR}$ is involved in mediating cell death in a variety of degenerative diseases. During adulthood, $p75^{NTR}$ expression is down-regulated in most brain areas but is rapidly induced in ischemia (stroke) and results in transient increased $p75^{NTR}$ expression and apoptosis, as do both peripheral and motor nerve lesions [10-12]. $p75^{NTR}$ is also up regulated in patients with MND [13], and in experimental allergic encephalomyelitiss (a model of multiple sclerosis; [14]). Intriguingly, in the basal forebrain and hippocampus, areas involved in learning and memory, $p75^{NTR}$ is highly expressed in aged rodents and in Alzheimer's patients, where extensive neural death is occurring [15, 16]. These data suggest that $p75^{NTR}$ is involved not only in normal developmental cell death, but may mediate the cell death occurring after injury or in neurodegenerative disease.

In work leading up to the present invention, the inventors sought to elucidate the region on $p75^{NTR}$ which mediates death signalling. The inventors surprisingly determined that the death signal is not the cytoplasmic motif known as the death domain [9] but is a region adjacent the membrane domain on $p75^{NTR}$. The identification of this region provides for an opportunity to modulate cell survival by antagonising the death signalling region or promoting apoptosis by providing cells with the genetic material to express the death signalling region adjacent, proximal or otherwise juxtaposed or associated with the membrane or to express the death signalling region in multimeric form.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention provides an isolated nucleic acid molecule comprising a sequence of nucleotides or complementary sequence of nucleotides which encodes an amino acid sequence which is capable of signalling, inducing or otherwise facilitating the death of a cell in which said amino acid sequence is adjacent, proximal or otherwise juxtaposed to the membrane of said cell or when said amino acid sequence is in multimeric form.

Another aspect of the present invention is directed to a nucleic acid molecule comprising a sequence of nucleotides or complementary sequence of nucleotides which encodes a peptide, polypeptide or protein capable of signalling, inducing or otherwise facilitating death of a cell in which it is expressed wherein said peptide, polypeptide or protein comprises a membrane associating portion and/or a multimer-forming portion and a portion which corresponds to all or part of the cytoplasmic region of $p75^{NTR}$ or a functional equivalent, derivative or homologue thereof.

Yet another aspect of the present invention contemplates homologues, analogues and derivatives of a nucleic acid molecule which encodes a peptide, polypeptide or protein which is capable of signalling inducing or otherwise facilitating death of a cell in which it is expressed wherein said peptide, polypeptide or protein comprises a membrane associating portion and/or a multimer-forming portion and a portion which corresponds to all or part of the cytoplasmic region of $p75^{NTR}$ or a functional equivalent, derivative or homologue thereof.

A further aspect of the present invention provides an isolated nucleic acid molecule comprising a sequence of nucleotides which encodes an amino acid sequence which inhibits or reduces $p75^{NTR}$-mediated cell death wherein said amino acid sequence is a soluble form of the $p75^{NTR}$ receptor corresponding to an intracellular region adjacent, proximal or otherwise juxtaposed to the membrane of said cell.

Still another aspect of the present invention provides a nucleic acid molecule comprising a nucleotide sequence or complementary nucleotide sequence which is substantially as set forth in SEQ ID NO:3 or is a nucleotide sequence capable of hybridizing to SEQ ID NO:3 or its complementary form under low stringency conditions or is a nucleotide sequence having at least 60% identity to SEQ ID NO:3.

Still yet another aspect of the present invention contemplates a nucleic acid molecule comprising a nucleotide sequence or a complementary form thereof, which nucleotide sequence encodes an amino acid sequence substantially as set forth in SEQ ID NO:4 or a derivative, homologue or chemical equivalent thereof or an amino acid sequence having at least 60% identity thereto.

Even yet another aspect of the present-invention provides a genetic construct comprising an isolated nucleic acid molecule which comprises a sequence of nucleotides which corresponds or is complementary to a death signal region from $p75^{NTR}$ or a homologue, analogue or derivative thereof.

Another aspect of the present invention contemplates an isolated peptide, polypeptide or protein comprising the cytoplasmic region of $p75^{NTR}$ which signals, induces or otherwise facilitates cell death when said peptide, polypeptide or protein is adjacent, proximal or otherwise juxtaposed to a membrane-associating region such as from $p75^{NTR}$ or other membrane molecule and/or said peptide, polypeptide or protein is capable of forming multimers or a derivative, homologue, chemical equivalent or analogue of said peptide, polypeptide or protein. This aspect of the present invention does not extend to the full length $p75^{NTR}$.

Still another aspect of the present invention contemplates a method for inhibiting, reducing or otherwise antagonising a $p75^{NTR}$-mediated death signal in a neural cell, said method comprising introducing a nucleic acid molecule capable of being expressed to an expression product which corresponds to a non-membrane associated form of the $p75^{NTR}$ death signal region or a derivative, functional equivalent or homologue thereof.

Yet another aspect of the invention contemplates a method for inhibiting, reducing or otherwise antagonising a $p75^{NTR}$-mediated death signal in a neural cell, said method comprising contacting a cell carrying a $p75^{NTR}$ with a death signal-inhibiting effective amount of a molecule capable of antagonising the death signal of $p75^{NTR}$ or a component of the death signalling pathway.

Even still another aspect of the present invention provides a biological composition comprising a genetic molecule capable of expressing a $p75^{NTR}$ death signal antagonist or a $p75^{NTR}$ death signal.

Another aspect of the present invention is directed to a biological composition comprising a molecule capable of antagonising $p75^{NTR}$-mediated death signalling of a cell.

Yet still another aspect of the present invention contemplates a method for modulating $p75^{NTR}$-mediated death signal in a neural cell, said method comprising administering an agent which antagonises or agonises cleavage of the extracellular domain of $p75^{NTR}$.

Still another aspect of the present invention provides a method for inhibiting, reducing or otherwise antagonising $p75^{NTR}$-mediated death signal in a neural cell, said method comprising administering a peptide, polypeptide or protein or analogues or mimetics thereof which correspond to a non-membrane associated form of the $p75^{NTR}$ death signal region or a derivative, functional equivalent or homologue thereof.

Another aspect of the present invention provides peptide antagonists of the $p75^{NTR}$ death signal or functional analogues or mimetics thereof.

The terms "c35" and "35 mer" are used interchangeably herein to refer to 35 amino acid domain juxtaposed to the membrane. When in soluble form, this peptide is referred to as soluble c35 or 35 mer. The nucleotide and amino acid sequence of c35 are shown in SEQ ID NO:7 and SEQ ID NO:8, respectively. The term "29 mer" refers to a truncated form of the 35 mer. Six amino acids have been deleted from the C-terminal end. The nucleotide and amino acid sequence of 29 mer are shown in SEQ ID NO:11 and SEQ ID NO:12, respectively. The present invention extends to isolated forms of c35 and the 29 mer, to compositions comprising same and to genetic sequences encoding same.

Figure 1:
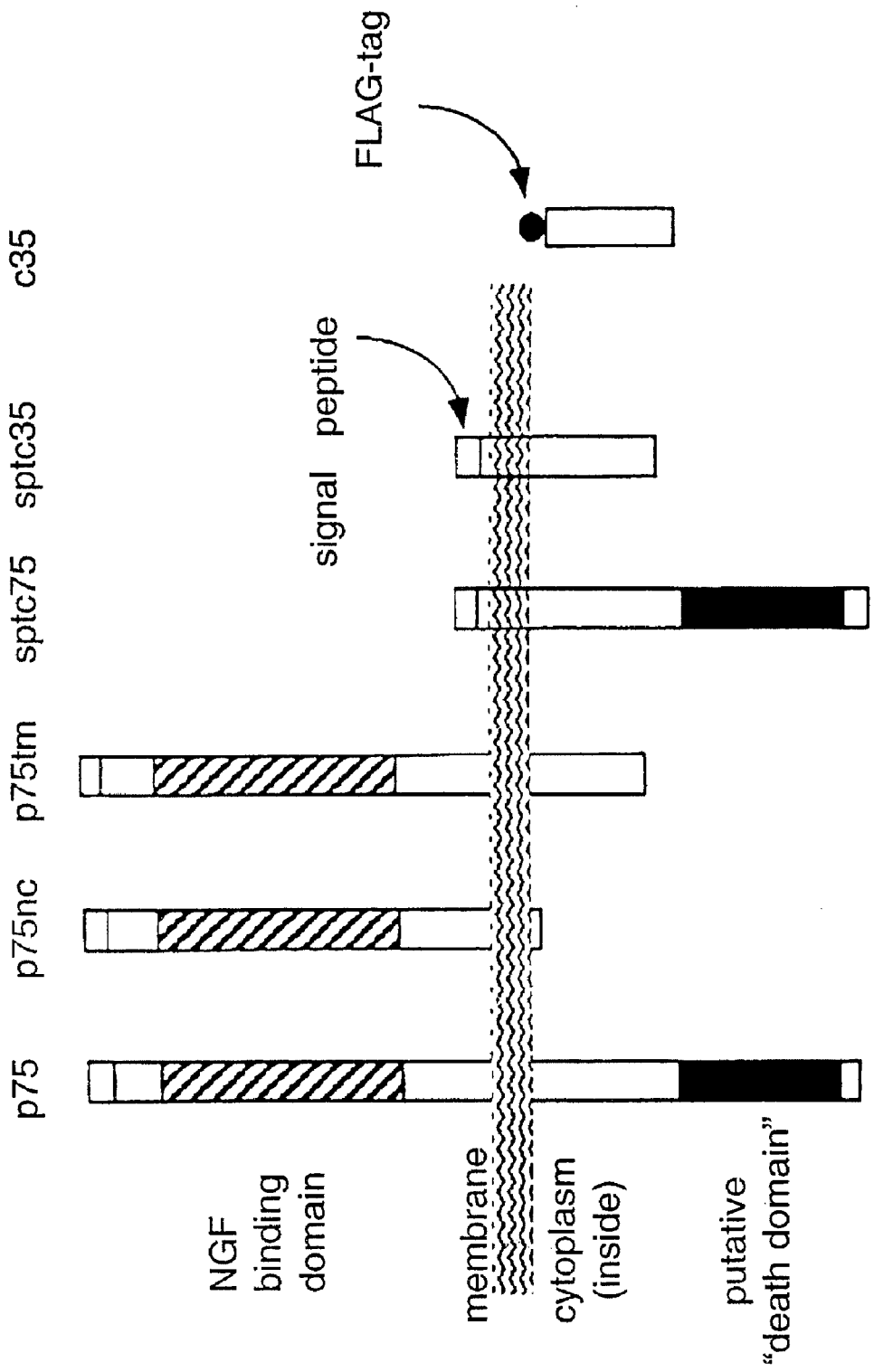
FIG. 1 is a diagrammatic representation showing plasmid constructs with and without the death signalling region. The black region is the putative "death domain" [9] but which is not directly involved in $p75^{NTR}$ mediated cell death.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

The present invention arose in part following an investigation of the neurotrophin receptor, p75$^{NTR}$, in its capacity as a death signalling protein. Although the p75$^{NTR}$ molecule comprises a putative death domain [9], in accordance with the present invention, this death domain is not directly associated with p75$^{NTR}$-mediated cell death. Rather, a region adjacent, proximal or otherwise juxtaposed to the membrane domain of p75$^{NTR}$ is required for cell death. The nucleotide and corresponding amino acid sequence of the death domain [9] is shown in SEQ ID NO:9 and SEQ ID NO:10, respectively.

Accordingly, one aspect of the present invention provides an isolated nucleic acid molecule comprising a sequence of nucleotides or complementary sequence of nucleotides which encode an amino acid sequence which is capable of signalling, inducing or otherwise facilitating the death of a cell in which said amino acid sequence is adjacent, proximal or otherwise juxtaposed to the membrane of said cell or when said amino acid sequence is in multimeric form.

Reference herein to the signalling, inducing or otherwise facilitating the death of a cell or a death signal is meant to be construed in its broadest sense meaning that the amino acid sequence plays a role in a pathway leading to cell death. The death signal may also be regarded as an apoptopic signal. Although not wishing to limit the present invention to anyone theory or mode of action, it is proposed herein that there is a pathway from p75$^{NTR}$ activation to caspase activation and cellular degeneration. p75$^{NTR}$-mediated cell death may also occur directly or indirectly via Bcl-2.

The present specification refers interchangeably to death signal, death signal region, signalling, inducing or otherwise facilitating the death of a cell and c35.

The nucleic acid molecule of the present invention may encode a non-full length p75$^{NTR}$ molecule although to facilitate cell death, the nucleic acid molecule must encode all or part of the cytoplasmic portion of the p75$^{NTR}$ molecule and a sufficient amount of the membrane domain such that the region referred to herein as the death signal is membrane associated. A "part" of the cytoplasmic domain of p75$^{NTR}$ includes all or a death-inducing functional part of a 35 amino acid region juxtaposed to the membrane domain. An example of a part of the 35 amino acid region is a truncated form. One such form is referred to herein as the "29 mer". Alternatively, the cytoplasmic domain of the p75$^{NTR}$ molecule is in multimeric form or capable of forming multimers. A multimer comprises two or more copies of the molecule such as a dimer, trimer or larger copy molecule.

The term "membrane associated" means that the death signal is adjacent, proximal or otherwise juxtaposed to the membrane of a cell expressing the nucleic acid molecule.

The "death signal region" and other related terms are used herein to describe functionally the region of the cytoplasmic portion of p75$^{NTR}$ which is adjacent, proximal or otherwise juxtaposed to a region of p75$^{NTR}$ which associates with the membrane or which cytoplasmic portion is in multimeric form. The death signal region is not the same portion of the molecules as the "death domain" [9] although there may be functional similarities in death signalling.

Accordingly, another aspect of the present invention is directed to a nucleic acid molecule comprising a sequence of nucleotides or complementary sequence of nucleotides which encodes a peptide, polypeptide or protein capable of signalling, inducing or otherwise facilitating death of a cell in which it is expressed wherein said peptide, polypeptide or protein comprises a membrane associating portion and/or a multimer-forming portion and a portion which corresponds to all or part of the cytoplasmic region of p75$^{NTR}$ or a functional equivalent, derivative or homologue thereof.

In order to signal, induce or otherwise facilitate death of a cell, the death signal region is preferably adjacent, proximal or otherwise juxtaposed to the cell membrane. This may be facilitated by modifying a peptide such that it associates with the membrane. One example of this type of modification is palmitoylation. This puts a palmitoyl group at the membrane (amino) end of the peptide.

Accordingly, another aspect of the present invention contemplates plamitoylated peptides, polypeptides or proteins comprising all or part of the death signal region of p75$^{NTR}$. Such peptides are particularly useful in promoting cell death.

The present invention also extends to multimeric forms of death signal peptides, polypeptides and proteins and attachments which facilitate same. A multimer comprises two or more molecules. The present invention also extends to cleavage forms of the full length p75$^{NTR}$ molecule.

In one embodiment, the membrane portion is derived from p75$^{NTR}$ or a functional equivalent, derivative or homologue thereof. In another embodiment, the membrane domain is from another molecule such as a receptor or other ligand binding molecule. Examples of receptors according to this aspect of the present invention include cytokine receptors (e.g. the Leukaemia Inhibitory Factor (L1F) receptor, interleukin receptor, and colony-stimulating factor receptors). Examples of ligand-binding molecules include immunoglobulins and T cell receptors.

When in multimeric form, the molecule-is only optionally associated with the membrane to effect cell death.

The nucleic acid molecule may comprise cDNA or genomic DNA or may comprise ribonucleotides such as mRNA. The nucleic acid molecule may be derived from a cDNA or genomic molecule encoding $p75^{NTR}$ or a derivative or homologue thereof or may be prepared by the stepwise addition of nucleotides in a defined sequence.

The nucleic acid molecule of the present invention may also be considered as corresponding to a "gene".

Reference herein to a "gene" is to be taken in its broadest context and includes:

(i) a classical genomic gene consisting of transcriptional and/or translational regulatory sequences and/or a coding region and/or nontranslated sequences (I.e. introns, 5'- and 3'-untranslated sequences);

(ii) mRNA or cDNA corresponding to the coding regions (I.e. exons) optionally comprising 5'- or 3'-untranslated sequences of the gene; or (iii) an amplified DNA fragment or other recombinant nucleic acid molecule produced in vitro and comprising all or a part of the coding region and/or 5'- or 3'-untranslated sequences of the gene.

The term "gene" is also used to describe synthetic or fusion molecules encoding all or part of a functional product. A functional product is one which comprises a sequence of nucleotides or is complementary to a sequence of nucleotides which encodes a functional death signal from $p75^{NTR}$ or its derivative or homologue.

The nucleotide sequence of the present invention may correspond to the cDNA or genomic sequence of a gene encoding $p75^{NTR}$ or a death signal region thereof or may be subjected to mutagenesis to produce single or multiple nucleotide substitutions, deletions and/or additions. Nucleotide insertional derivatives of the nucleic acid molecule of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

Accordingly, another aspect of the present invention contemplates homologues, analogues and derivatives of a nucleic acid molecule which encodes a peptide, polypeptide or protein which is capable of signalling, inducing or otherwise facilitating death of a cell in which it is expressed wherein said peptide, polypeptide or protein comprises a membrane associating portion and/or multimer-forming portion and a portion which corresponds to all or part of the cytoplasmic region of $p75^{NTR}$ or a functional equivalent, derivative or homologue thereof.

For the present purpose, "homologues" of a nucleic acid molecule as herein defined or of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleic acid molecule as herein defined or of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleic acid molecule as herein defined or of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

In one embodiment, the derivatives encode a peptide, polypeptide or protein which induces cell death. In another embodiment, the derivatives do not induce cell death but antagonise the death signal.

According to this latter embodiment, there is provided an isolated nucleic acid molecule comprising a sequence of nucleotides which encodes an amino acid sequence which inhibits or reduces $p75^{NTR}$-mediated cell death wherein said amino acid sequence is a soluble form of the $p75^{NTR}$ receptor corresponding to an intracellular region adjacent, proximal or otherwise juxtaposed to the membrane of said cell.

The nucleic acid molecule of the present invention may be based on a nucleotide sequence of the gene or cDNA encoding $p75^{NTR}$ from any animal such as from mammals. Preferred mammals include humans, primates, livestock animals (e.g. cows, sheep, horses, pigs, donkeys, goats), laboratory test animals (e.g. rabbits, mice, rats, guinea pigs, hamsters), companion animals (e.g. dogs, cats) and captive wild animals.

A particularly preferred sequence is from human or primate or murine $p75^{NTR}$.

Although not wishing to limit the present invention to anyone theory or mode of action, it is proposed that the extracellular domain of $p75^{NTR}$ may be cleaved off resulting in active death signal (see Zupan et at [20]). Accordingly, by antagonizing cleavage, cell death may be prevented or at least delayed or inhibited. Conversely, for targeted cancer cells, an agonist of $p75^{NTR}$ extracellular domain cleavage would promote cell death.

Accordingly, another aspect of the present invention contemplates a method for modulating $p75^{NTR}$-mediated death signal in a neural cell, said method comprising administering an agent which antagonises or agonises cleavage of the extracellular domain of $p75^{NTR}$.

Preferably, to prevent neural cell death, extracellular $p75^{NTR}$ cleavage is antagonised.

The present invention is exemplified using a nucleotide sequence from rat p75$^{NTR}$ cDNA. This is done, however, with the understanding that the nucleotide sequence may be from p75$^{NTR}$ genomic or cDNA from any animal.

Accordingly, another aspect of the present invention provides a nucleic acid molecule comprising a nucleotide sequence or a complementary form thereof wherein said nucleotide sequence is capable of hybridizing to SEQ ID NO:1 or a complementary form thereof under low stringency conditions, such as at 42° C.

The nucleotide sequence set forth in SEQ ID NO:1 is the cDNA sequence encoding p75$^{NTR}$. The nucleic acid molecule according to this aspect of the present invention does not extend to the full length p75$^{NTR}$ cDNA sequence but comprises a portion which encodes an amino acid sequence which signals, induces or otherwise facilitates cell death when associated with a membrane portion of p75$^{NTR}$ or other molecules.

Accordingly, another aspect of the present invention provides a nucleic acid molecule comprising a nucleotide sequence or complementary nucleotide sequence which is substantially as set forth in SEQ ID NO:7 or is a nucleotide sequence capable of hybridizing to SEQ ID NO:7 or a complementary form thereof under low stringency conditions such as at 42° C. or is a nucleotide sequence having at least 60% identity to SEQ ID NO:7.

The nucleotide sequence set forth in SEQ ID NO:7 is the death signal defined herein associated with p75$^{NTR}$. This sequence encodes a 35 amino acid region also referred to herein as "c35". Truncated forms of c35 are also contemplated by the present invention such as a 25-30 amino acid molecules. One particular example is a 29 mer which lacks carboxy terminal amino acids 30 to 35. As stated above, the present invention extends to palmitoylated c35 and its derivatives as well as molecules fused with molecules to facilitate membrane passage such as penetratin and the TAT protein from human immunodeficiency virus (HIV).

Reference herein to a low stringency such as at 42° C. includes and encompasses from at least about 0% v/v to at least about 15% v/v formamide and from at least about 1 M to at least about 2M salt for hybridisation, and at least about 1 M to at least about 2M salt for washing conditions. Alternative stringency conditions may be applied where necessary, such as medium stringency, which includes and encompasses from at least about 16%-v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01 M to at least about 0.15M salt for hybridisation, and at least about 0.01 M to at least about 0.15M salt for washing conditions. Preferably, low stringency is determined at 42° C.

The present invention further contemplates a nucleic acid molecule comprising a nucleotide sequence or a complementary form thereof, which nucleotide sequence encodes an amino acid sequence substantially as set forth in SEQ ID NO:8 or a derivative, homologue or chemical equivalent thereof or an amino acid sequence having at least 60% identity thereto.

The amino acid sequence of SEQ ID NO:8 corresponds to the amino acid sequence of the p75$^{NTR}$ death signal.

The term "identity" as used herein includes exact identity between compared sequences at the nucleotide or amino acid level. Where there is non-identity at the nucleotide level, the term "similarity" may also be used and includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch [17]. Gap reads a scoring matrix that contains values for every possible GCG symbol match. GAP is available on ANGIS (Australian National Genomic Information Service) at website "mel1.angis.org.au."

The present invention further comprises a nucleic acid molecule comprising the nucleotide sequence:

$\{n_i\ \text{-}\ \text{-}\ \text{-}\ n_x\}_b\ a\{n'_1\ \text{-}\ \text{-}\ \text{-}\ n'_y\}_c\ a\{n''_1\ \text{-}\ \text{-}\ \text{-}\ n''_z\}_d$ wherein $\{n_1\ \text{-}\ \text{-}\ \text{-}\ n_x\}$ is a sequence of x nucleotides encoding an extracellular portion of a receptor or ligand-binding molecule;

$\{n'_1\ \text{-}\ \text{-}\ \text{-}\ n'_y\}$ is a sequence of y nucleotides encoding a transmembrane peptide, polypeptide or protein or a molecule capable of inducing multimerisation;

$\{n''_1\ \text{-}\ \text{-}\ \text{-}\ n''_z\}$ is a sequence of z nucleotides comprising a nucleotide sequence substantially as set forth in SEQ ID NO:7 or a nucleotide sequence encoding an amino acid sequence substantially as set forth in SEQ ID NO:8 or a nucleotide sequence capable of hybridizing to SEQ ID NO:7 or a complementary form thereof under low stringency conditions such as at 42° C. or a nucleotide sequence having at least 60% identity to SEQ ID NO:7;

b, c and d may be the same or difference and each is 0, 1 or >1;

x, y and z may be the same or different and each is 0, 1 or >1;

a is a nucleotide bond;

wherein when c is 1 or >1 and d is 1 or >1 and wherein when the molecule is expressed in a neural cell, the expression product signals, induces or otherwise facilitates cell death.

Preferably, $\{n_1\ \text{-}\ \text{-}\ \text{-}\ n_x\}$ comprises the nucleotide sequence substantially as set forth in SEQ ID NO:3 or is a nucleotide sequence having at least about 60% identity thereto or is capable of hybridizing to SEQ ID NO:3 or its complementary form under low stringency conditions such as at 42° C.

Preferably, $\{n'_1\ \text{-}\ \text{-}\ \text{-}\ n'_y\}$ comprises the nucleotide sequence substantially as set forth in SEQ ID NO:5 or is a nucleotide sequence having at least about 60% identity thereto or is capable of hybridizing to SEQ ID NO:5 or its complementary form under low stringency conditions such as at 42° C.

The nucleotide sequences $\{n_1\ \text{-}\ \text{-}\ \text{-}\ n_x\}$, $\{n'_1\ \text{-}\ \text{-}\ \text{-}\ n'_y\}$ and $\{n''_1\ \text{-}\ \text{-}\ \text{-}\ n''_z\}$ may be in any order and in any combination.

For the production of a recombinant peptide, polypeptide or protein comprising the death signal, the nucleic acid molecule of the present invention is placed, in the sense orientation, in operable connection with a suitable promoter sequence and introduced into a suitable expression system, for example a bacterial, yeast, baculovirus, plant, animal or other expression system.

Accordingly, a further aspect of the present invention provides a genetic construct comprising an isolated nucleic acid molecule which comprises a sequence of nucleotides which corresponds or is complementary to a death signal region from p75$^{NTR}$ or a homologue, analogue or derivative thereof.

According to this embodiment, the coding region of the death signal from p75$^{NTR}$ may be placed in operable connection with a promoter sequence such that a gene product is capable of being expressed under the control of said promoter sequence.

Optionally, said genetic construct further comprises a terminator sequence.

In the present context, the term "in operable connection with" is used to indicate that expression of the isolated nucleotide sequence is under the control of the promoter sequence with which it is connected.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants.

Examples of terminators particularly suitable for use in the genetic constructs of the present invention include the SV40 polyadenylation signal, amongst others.

Reference herein to a "promoter" is to be taken in its broadest context and includes the transcriptional regulatory sequences of a classical genomic gene, including the TATA box which is required for accurate transcription initiation in eukaryotic cells, with or without a CCAAT box sequence and additional regulatory elements (i.e., upstream activating sequences, enhancers and silencers). For expression in prokaryotic cells, such as bacteria, the promoter should at least contain the −35 box and −10 box sequences.

A promoter is usually, but not necessarily, positioned upstream or 5', of the nucleotide sequence encoding the death signal of p75$^{NTR}$, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of an isolated nucleic acid molecule, in a cell, such as a plant, animal, insect, fungal, yeast or bacterial cell. Preferred promoters may contain additional copies of one or more specific regulatory elements, to further enhance expression of a nucleic acid molecule which expression it regulates and/or to alter the spatial expression and/or temporal expression of same. For example, regulatory elements which confer copper inducibility may be placed adjacent to a heterologous promoter sequence driving expression of a nucleic acid molecule, thereby conferring copper inducibility on the expression of said molecule.

Placing an isolated nucleic acid molecule under the regulatory control of a promoter sequence means positioning said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include viral, fungal, bacterial, animal and plant derived promoters capable of functioning in plant, animal, insect, fungal, yeast or bacterial cells. The promoter may regulate the expression of the nucleic acid molecule constitutively, or differentially with respect to the tissue in which expression occurs or, with respect to the developmental stage at which expression occurs, or in response to external stimuli such as physiological stresses, or plant pathogens, or metal ions, amongst others.

Preferably, the promoter is capable of regulating expression of a nucleic acid molecule in a yeast or bacterial cell.

Examples of preferred promoters include the bacteriophage T7 promoter, bacteriophage T3 promoter, SP6 promoter, lac promoter, tac promoter, SV40 early promoter, and the like.

The genetic construct contemplated herein is introduced into a suitable expression system for a time and under conditions sufficient for expression of said death signal or inhibitor portion from p75$^{NTR}$ to occur.

The genetic construct may also comprise a nucleotide sequence corresponding to all or part of the membrane domain of p75$^{NTR}$ or other membrane molecules. Accordingly, a further aspect of the invention contemplates a recombinant peptide, polypeptide or protein produced by expressing the isolated nucleic acid molecule herein described in a suitable host cell. The present invention extends also to a synthetic peptide fragment of said recombinant gene product.

The present invention further contemplates an isolated peptide, polypeptide or protein comprising the cytoplasmic region of p75$^{NTR}$ which signals, induces or otherwise facilitates cell death when said peptide, polypeptide or protein is adjacent, proximal or otherwise juxtaposed to a membrane-associating region such as from p75$^{NTR}$ or other membrane molecule and/or is in multimeric form or a derivative, homologue, chemical equivalent or analogue of said peptide, polypeptide or protein. This aspect of the present invention does not extend to the full length p75$^{NTR}$.

Suitable molecules according to this aspect of the present invention include a peptide, polypeptide or protein corresponding to a soluble form of the death signalling region of p75$^{NTR}$ or a molecule capable of antagonising that region or a component of the death signalling pathway. An example of a possible component of the death signalling pathway is Bcl-2.

The peptide, polypeptide or protein of this aspect of the present invention is useful inter alia as a therapeutic molecule to antagonise p75$^{NTR}$-mediated death signalling. For example, the peptide, polypeptide or protein may themselves be administered to directly antagonise p75$^{NTR}$-mediated death signalling or the peptide, polypeptide or protein may need to be chemically modified to facilitate penetration into the cell. One such chemical modification is fusion to or co-expression with penetratin or the TAT protein from HIV. Alternatively, the death signalling region of p75$^{NTR}$ may be used to screen for antagonists of this region. Such antagonists may, for example, be identified following natural product screening or the screening of chemical libraries. For natural product screening suitable environments include, but are not limited to, plants, bacteria and other microorganisms, river and sea beds, coral and arctic or antarctic regions. The present invention also contemplates antagonists directed to other components of the p75$^{NTR}$-mediated death signalling pathway. Such components to be targeted include but are not limited to Bcl-2 or related or homologous molecules. Preferably, for peptides, polypeptides and proteins designed to induce cell death, the molecules are palmitoylated.

Preferably, the peptide, polypeptide or protein comprises an amino acid sequence substantially as set forth in SEQ ID NO:8 or an amino acid sequence having at least 60% identity thereto or a chemical equivalent, derivative, homologue or analogue of said peptide, polypeptide or protein.

The term "isolated" means that the peptide, polypeptide or protein of the present invention is provided in a form which is distinct from that which occurs in nature, preferably wherein one or more contaminants have been removed. Accordingly, the isolated peptide, polypeptide or protein of the invention may be partially-purified or substantially pure, in which a substantial amount of the contaminants have been removed or in sequencably pure or substantially homogeneous form.

The term "sequencably pure" means that the isolated peptide, polypeptide or protein is provided in a form which is sufficiently purified to facilitate amino acid sequence determination using procedures known to those skilled in the art.

The term "substantially homogeneous" means that the isolated peptide, polypeptide or protein of the present invention is at least about 95% free of contaminants, more preferably at least about 99% free of contaminants, including 100% purity.

The present invention extends to a range of derivatives and chemical analogues of the peptide, polypeptide or protein.

Furthermore, the amino acids of a homologous polypeptide may be replaced by other amino acids having similar properties, for example hydrophobicity, hydrophilicity, hydrophobic moment, charge or antigenicity, and so on.

"Analogues" encompass death signal containing peptides, polypeptides or proteins which are at least about 60% identical to the p75$^{NTR}$ death signal sequence (SEQ ID NO:8), notwithstanding the occurrence of any non-naturally occurring amino acid analogues therein. "Analogues" also encompass polypeptide mimotypes.

The term "derivative" in relation to a peptide, polypeptide or protein shall be taken to refer hereinafter to mutants, parts or fragments derived from the functional p75$^{NTR}$ molecule or death signal region thereof or derivatives thereof which mayor may not possess the death signal activity of the functional p75$^{NTR}$. Derivatives include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are particularly contemplated by the present invention. Additionally, derivatives of the peptide, polypeptide or protein described herein comprise fragments or parts of an amino acid sequence disclosed herein are within the scope of the invention, as are homopolymers or heteropolymers comprising two or more copies of the subject polypeptides. Procedures for derivatizing peptides are well-known in the art.

A homologue, analogue or derivative of SEQ ID NO:2 or SEQ ID NO:8 may comprise an amino acid substitution or said SEQ ID NO:2 or SEQ ID NO:8 may encompass amino acid alterations in which an amino acid is replaced with a different naturally-occurring or a non-conventional amino acid residue. Such substitutions may be classified as "conservative", in which case an amino acid residue contained in a phospholipase inhibitory protein is replaced with another naturally-occurring amino acid of similar character, for example Gly←→Ala, Val←→Ile←→Leu, Asp←→Glu, Lys←→Arg, Asn←→Gln or Phe←→Trp←→Tyr.

Substitutions encompassed by the present invention may also be "non-conservative", in which an amino acid residue which is present in a phospholipase inhibitory protein is substituted with an amino acid having different properties, such as a naturally-occurring amino acid from a different group (e.g., substituted a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Naturally-occurring amino acids include those listed in Table 1. Non-conventional amino acids encompassed by the invention include, but are not limited to those listed in Table 2.

Amino acid deletions will usually be of the order of about 1-10 amino acid residues, while insertions may be of any length. Deletions and insertions may be made to the N-terminus, the C-terminus or be internal deletions or insertions. Generally, insertions within the amino acid sequence will be smaller than amino- or carboxyl-terminal fusions and of the order of 1-4 amino acid residues.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Ley | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-Conventional Amino Acid | Code | Non-Conventional Amino Acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |

TABLE 2-continued

| Non-Conventional Amino Acid | Code | Non-Conventional Amino Acid | Code |
|---|---|---|---|
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methyl asparagine | Dmasn | α-methyl-α-napthylalanine | Manap |
| D-α-methylaspartate | Dmasp | α-methyl penicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methyl asparagine | Masn |
| L-α-methylasparate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methyl isoleucine | Mile | N-(2-methylthioethyl)glycine | Nmet |
| L-α-methylleucine | Mleu | L-α-methyllysine | Mlys |
| L-α-methylmethionine | Mmet | L-α-methyl norleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomo phenylalanine | Nmhphe |

TABLE 2-continued

| Non-Conventional Amino Acid | Code | Non-Conventional Amino Acid | Code |
|---|---|---|---|
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenylethylamino)cyclopropane | Nmbc | | |

The present invention provides therefore, peptides, polypeptides and proteins which inhibit p75$^{NTR}$ death signalling and/or cleavage of extracellular domain of p75$^{NTR}$ Accordingly, another aspect of the present invention contemplates a method for inhibiting, reducing or otherwise antagonising p75$^{NTR}$-mediated death signal in a neural cell, said method comprising administering a peptide, polypeptide or protein or analogues or mimetics thereof which correspond to a non-membrane associated form of the p75$^{NTR}$ death signal region or a derivative, functional equivalent or homologue thereof.

Yet another aspect of the present invention is directed to peptide antagonists of the p75$^{NTR}$ death signal or functional analogues or mimetics thereof.

The present invention provides for a method of treatment or prophylaxis of disease conditions associated with neural death or where cell death is to be promoted such as in treating or preventing cancer growth and/or development.

In one embodiment, it has been determined in accordance with the present invention that expression of a nucleic acid molecule encoding only death signal and not adjacent, proximal or juxtaposed to a membrane-associating sequence results in antagonising of the death signal. According to this embodiment, the present invention contemplates a method for inhibiting, reducing or otherwise antagonising a p75$^{NTR}$-mediated death signal in a neural cell, said method comprising introducing a nucleic acid molecule capable of being expressed to an expression product which corresponds to a non-membrane associated form of the p75$^{NTR}$ death signal region or a derivative, functional equivalent or homologue thereof.

In a related embodiment there is provided a method for inhibiting, reducing or otherwise antagonising a p75$^{NTR}$-mediated death signal in a neural cell, said method comprising contacting a cell carrying a p75$^{NTR}$ with a death signal-inhibiting effective amount of a molecule capable of antagonising the death signal of p75$^{NTR}$ or a component of the death signalling pathway. This aspect of the present invention is useful for the treatment of a range of neurodegenerative diseases such as cerebral palsy, trauma induced paralysis, vascular ischaemia associated with stroke, neural tumours, motor neurone disease, Parkinson's disease, Huntington's disease, Alzheimer's disease, multiple sclerosis and peripheral neuropathies associated with diabetes, heavy metal or alcohol toxicity, renal failure and/or infectious diseases such as herpes, rubella, measles, chicken pox, HIV and/or HTLV-1. This aspect is also useful for treating neurons or glia damaged by trauma or disease.

Alternatively, the method is aimed at targeting certain cells such as cancer cells wherein expression is required of a death signal from p75$^{NTR}$ or a derivative, functional equivalent or homologue thereof adjacent, proximal or otherwise juxtaposed to a membrane-associating portion of p75$^{NTR}$ or other membrane molecules or is in multimeric form. The nucleic acid molecule may require modification to ensure appropriate targeting to the cell or the nucleic acid molecule may be injected directly into cancerous tissue.

Another aspect of the present invention provides a biological composition comprising a genetic molecule capable of being expressed into a p75$^{NTR}$ death signal antagonist or a p75$^{NTR}$ death signal. The biological composition further comprises one or more pharmaceutically acceptable carriers and/or diluents. The nucleic acid molecules according to this aspect of the present invention may be naked nucleic acid molecules or contained or associated with a viral vector or other suitable delivery mechanism. Another aspect of the present invention is directed to a biological composition comprising a molecule capable of antagonising p75$^{NTR}$-mediated death signalling of a cell.

Suitable molecules according to this aspect of the present invention are as contemplated above and include a peptide, polypeptide or protein comprising a soluble form of the p75$^{NTR}$ death signalling region or an antagonist of a component of the p75$^{NTR}$ death signalling pathway. The present invention is also useful as a culture agent such as preventing or reducing the death of cells in vitro. The present invention is particularly useful in vitro when used in combination with L1F. Even more particularly, the present invention is useful for culturing recombinant cell lines. The present invention also provides for the use of the death signal of p75$^{NTR}$ in the manufacture of a medicament for the treatment of neurodegenerative diseases in animals. Preferred animals include humans, primates, livestock animals, laboratory test animals, companion animals and captive wild animals. The present invention is further described by the following non-limiting Examples.

EXAMPLE 1

The aim of this example was to determine the protein domains on p75$^{NTR}$ responsible for death signalling.

In order to investigate how p75$^{NTR}$ signals neural death, the inventors devised a robust in vitro assay for p75$^{NTR}$ induced death. Plasmid expression constructs were microinjected into individual neurons in the presence of the growth factor L1F, and the survival of the neurons expressing the different plasmids was determined. A series of plasmid constructs which encode incomplete p75$^{NTR}$ proteins were made (see FIG. 1) and the ability of each protein to signal death when over expressed was assessed.

The p75$^{NTR}$ protein is a transmembrane protein comprised of a large extracellular domain with four cysteine rich motifs responsible for interacting with soluble growth factors, and a short cytoplasmic, intracellular tail. The cytoplasmic domain does not contain a kinase domain but contains a domain with significant homology to a motif known as a "death domain" (SEQ ID NO:9, SEQ ID NO:10), found in apoptosis-inducing Tumour Necrosis Factor Receptors (TNFR) and TNFR-associating death-effector proteins [9].

Figure 2:
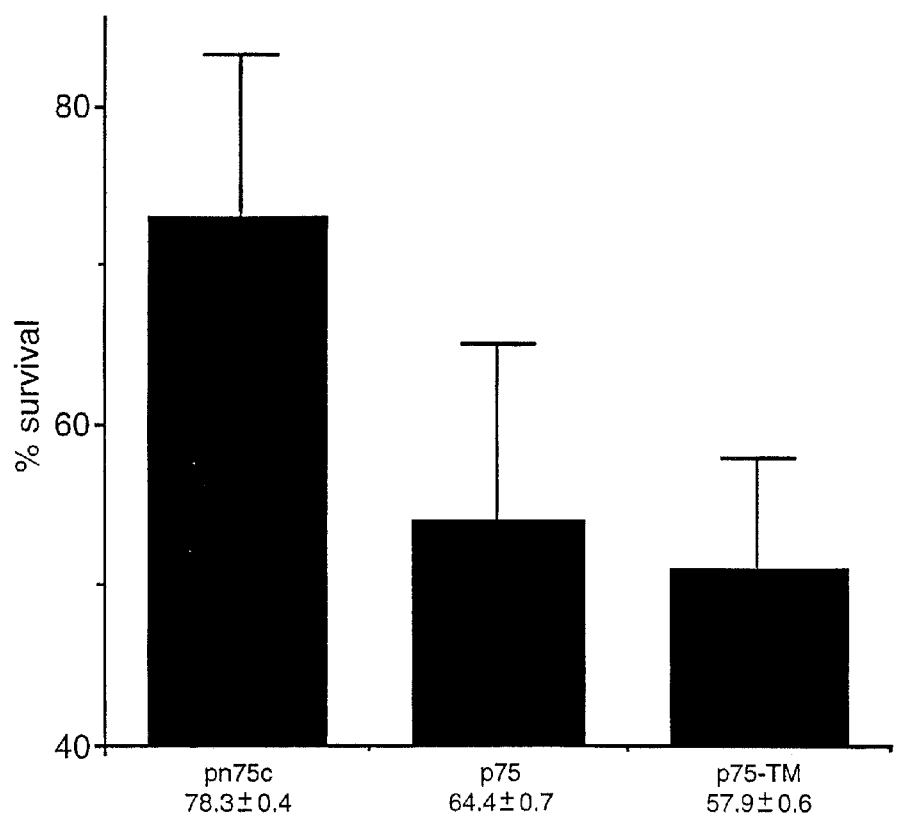
FIG. 2 is a graphical representation showing survival of DRG neurons 17 hours after microinfection and cultured in L1F. The data show that the amino acid domain juxtaposed to the membrane is required for death signalling rather than the putative "death domain" [9].

Using expression plasmids of p75$^{NTR}$ proteins deleted for either the entire cytoplasmic domain (p75nc) or a significant portion of the cytoplasmic domain including the entire death domain (p75tm), the inventors found that the cytoplasmic domain is responsible for death signalling. Surprisingly, the intracellular 35 amino acid domain juxtaposed to the membrane, and not the death domain, is responsible for death signalling (FIG. 2). This region of the p75$^{NTR}$ protein shows no homology to other death inducing proteins or to known functional motifs.

To further investigate the domain required for death signalling the inventors made constructs expressing p75$^{NTR}$ proteins deleted for the extracellular domain or the extracellular and transmembrane domains. Proteins without extracellular domains retain the signal peptide which is responsible for correctly transporting the protein into the cell membrane. Proteins without transmembrane domains are expressed free in the cytoplasm of the cell and are epitope tagged with a FLAG motif for detection. The inventors found that the extracellular domain of p75$^{NTR}$ had a significant inhibitory effect of the ability of the cytoplasmic domain to signal cell death.

Figure 3:
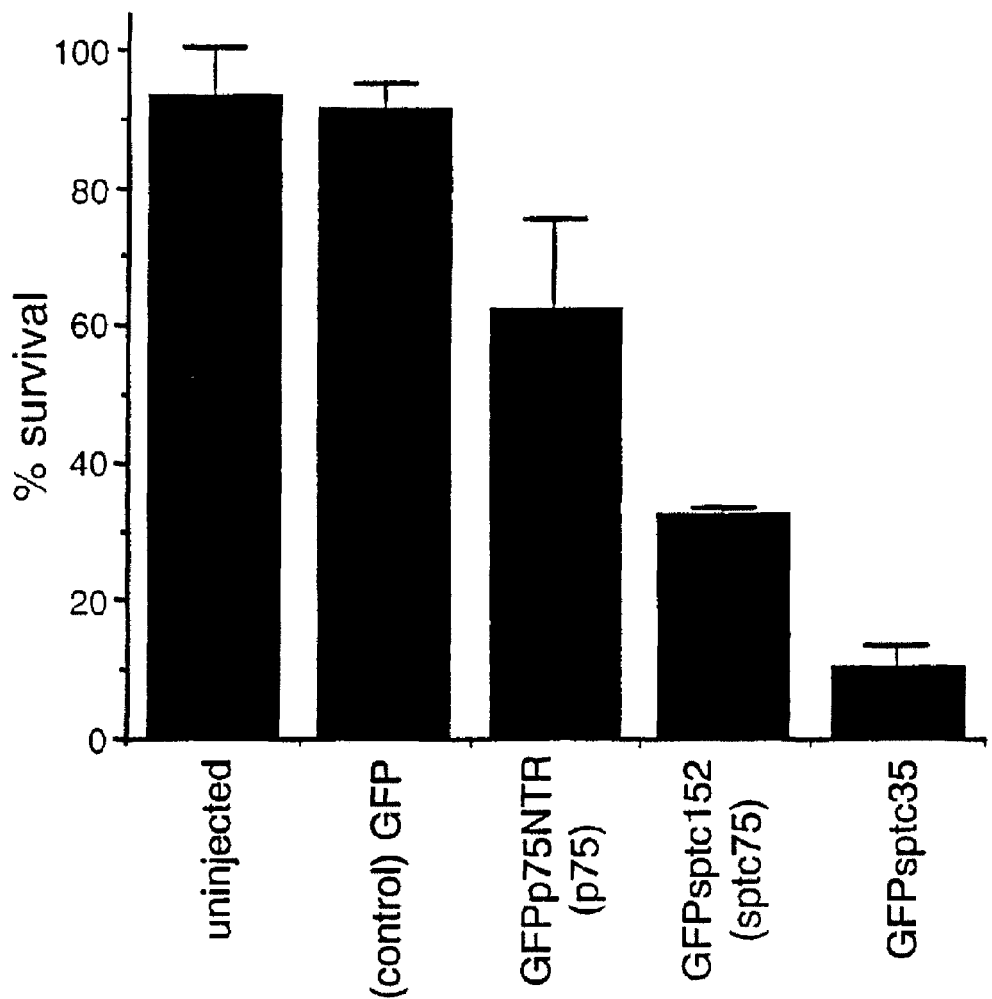
FIG. 3 is a graphical representation showing DRG survival 16 hours after microinjection and cultured in L1F. The data show that over 90% of cells die when expressing the death signal linked to the membrane.
Figure 4:
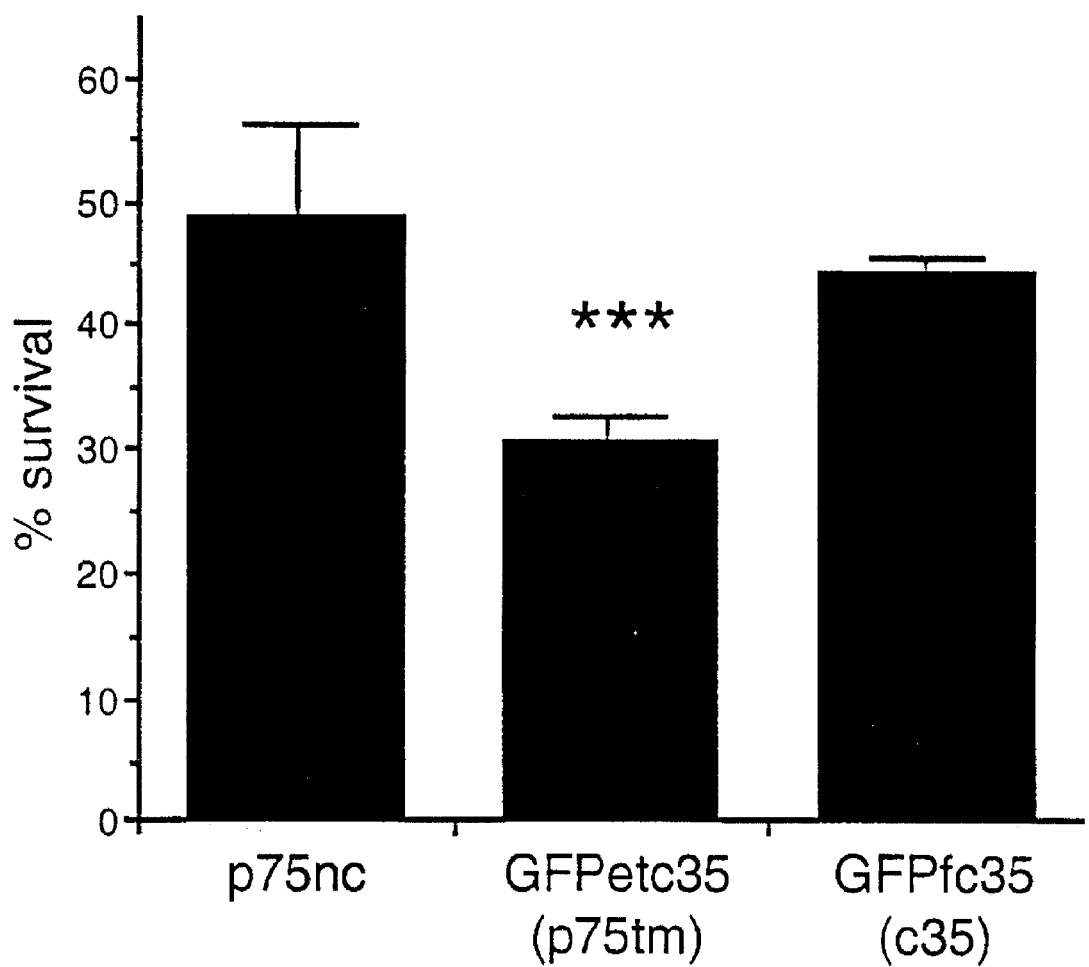
FIG. 4 is a graphical representation showing DRG survival 20 hours after microinjection and cultured in L1F. These data show that when the death signal is not associated with the membrane, that the ability to induce death is removed.

Furthermore, the membrane linked 35 amino acid cytoplasmic domain (c35) was a potent stimulant of neural death with over 90% of cells injected with the plasmid dead after 16 hours (FIG. 3). However, if the cytoplasmic 35 amino acid domain is not associated with the membrane, the ability of the domain to induce death is removed (FIG. 4).

These results indicate that the domain responsible for death induction is within the first 35 amino acids of the cytoplasmic tail but that the transmembrane domain, or at least association with the membrane, is required for death-signal activation. This may be related to the ability of the transmembrane protein to more efficiently form death-signal inducing multimers, or that the position of the p75$^{NTR}$ protein in relation to other membrane-bound accessory molecules might be important in initiating death signalling.

Figure 5:
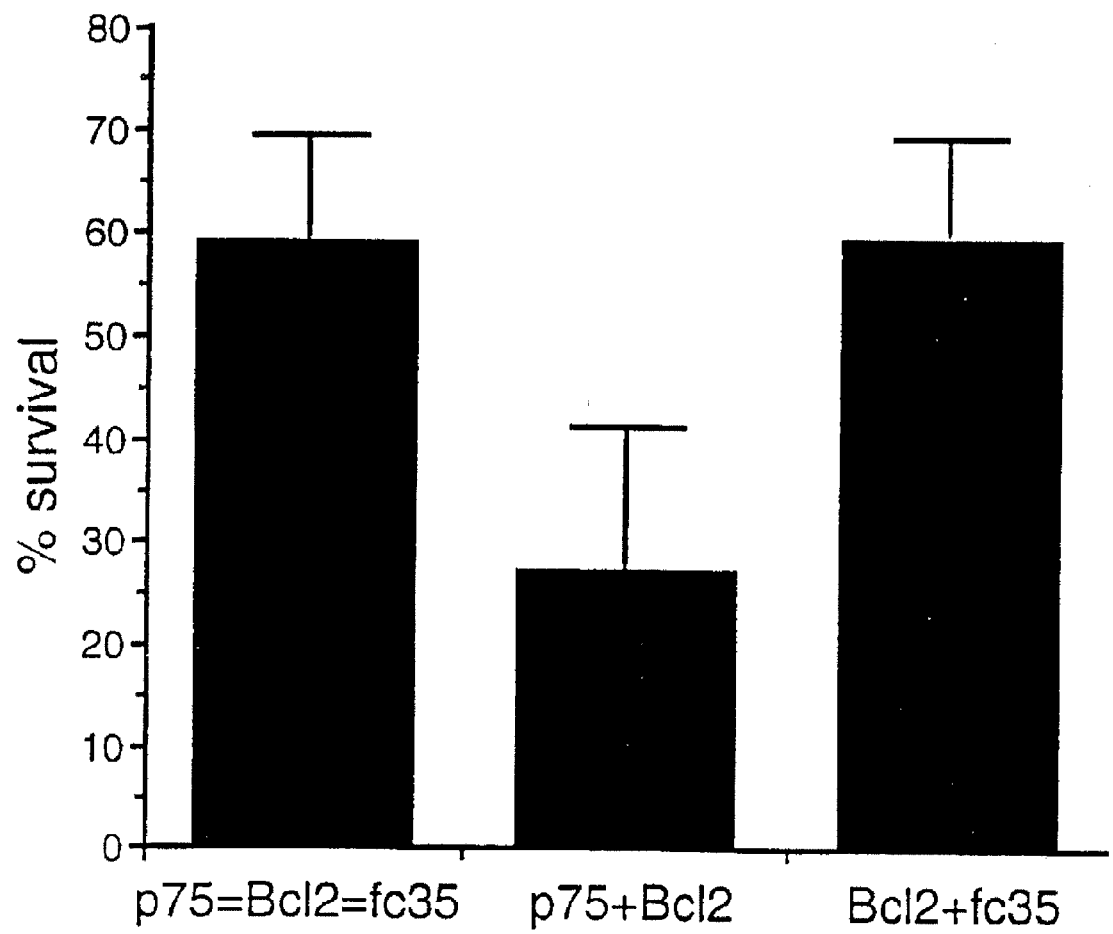
FIG. 5 is a graphical representation showing that the c35 soluble protein (i.e. p75$^{NTR}$ death signal region) inhibits death signalling mediated by p75$^{NTR}$.

The inventors hypothesised that the free cytoplasmic expressed 35 amino acid domain might be able to interfere with death signalling from full length p75$^{NTR}$ proteins by a dominant-negative mechanism, and attempted to inhibit the death by co-expressing the proteins. Given the results presented below regarding the ability of overexpression of Bcl-2 to enhance p75$^{NTR}$ killing, this paradigm was used to test the ability of the c35 protein to inhibit death signalling. The inventors found that indeed the expression of the c35 protein was able to inhibit this killing (FIG. 5). This further indicates that p75$^{NTR}$ signals killing via interaction of an accessory molecule to a motif within the first 35 amino acids of the cytoplasmic domain.

EXAMPLE 2

The aim of this example is to determine the minimum number of amino acid residues on c35 require to mediate death signalling. A series of deletion and truncation mutants in the c35 region are produced and tested for the ability to induce death signalling.

A series of deletion and truncation mutants in the c35 region are produced and tested for the ability to induce death signalling.

The deletion mutants from the membrane distal end are as follows:

```
                                     (SEQ ID NO: 13)
    KRWNSCKQNKQGANSRPVNQTPPPEGEKLHSDSG;

(SEQ ID NO: 14)
    KRWNSCKQNKQGANSRPVNQTPPPEGEKLHSDS;

(SEQ ID NO: 15)
    KRWNSCKQNKQGANSRPVNQTPPPEGEKLHSD;

(SEQ ID NO: 16)
    KRWNSCKQNKQGANSRPVNQTPPPEGEKLHS;

(SEQ ID NO: 17)
    KRWNSCKQNKQGANSRPVNQTPPPEGEKLH;

(SEQ ID NO: 18)
    KRWNSCKQNKQGANSRPVNQTPPPEGEKL;

(SEQ ID NO: 19)
    KRWNSCKQNKQGANSRPVNQTPPPEGEK;

(SEQ ID NO: 20)
    KRWNSCKQNKQGANSRPVNQTPPPEGE;

(SEQ ID NO: 21)
    KRWNSCKQNKQGANSRPVNQTPPPEG;

(SEQ ID NO: 22)
    KRWNSCKQNKQGANSRPVNQTPPPE;

(SEQ ID NO: 23)
    KRWNSCKQNKQGANSRPVNQTPPP;

(SEQ ID NO: 24)
    KRWNSCKQNKQGANSRPVNQTPP;

(SEQ ID NO: 25)
    KRWNSCKQNKQGANSRPVNQTP;

(SEQ ID NO: 26)
    KRWNSCKQNKQGANSRPVNQT;

(SEQ ID NO: 27)
    KRWNSCKQNKQGANSRPVNQ;

(SEQ ID NO: 28)
    KRWNSCKQNKQGANSRPVN;

(SEQ ID NO: 29)
    KRWNSCKQNKQGANSRPV;

(SEQ ID NO: 30)
    KRWNSCKQNKQGANSRP;

(SEQ ID NO: 31)
    KRWNSCKQNKQGANSR;

(SEQ ID NO: 32)
    KRWNSCKQNKQGANS;

(SEQ ID NO: 33)
    KRWNSCKQNKQGAN;

(SEQ ID NO: 34)
    KRWNSCKQNKQGA;

(SEQ ID NO: 35)
    KRWNSCKQNKQG;

(SEQ ID NO: 36)
    KRWNSCKQNKQ;

(SEQ ID NO: 37)
    KRWNSCKQNK;

(SEQ ID NO: 38)
    KRWNSCKQN;

(SEQ ID NO: 39)
    KRWNSCKQ;

(SEQ ID NO: 40)
    KRWNSCK;

(SEQ ID NO: 41)
    KRWNSC;

(SEQ ID NO: 42)
    KRWNS;
```

```
                                   (SEQ ID NO: 43)
KRWN;

KRW;

KR;
and

K.
```

The deletion mutants from the membrane proximal end are as follows:

```
                                           (SEQ ID NO: 44)
RWNSCKQNKQGANSRPVNQTPPPEGEKLHSDSGI;

(SEQ ID NO: 45)
WNSCKQNKQGANSRPVNQTPPPEGEKLHSDSGI;

(SEQ ID NO: 46)
NSCKQNKQGANSRPVNQTPPPEGEKLHSDSGI;

(SEQ ID NO: 47)
SCKQNKQGANSRPVNQTPPPEGEKLHSDSGI;

(SEQ ID NO: 48)
CKQNKQGANSRPVNQTPPPEGEKLHSDSGI;

(SEQ ID NO: 49)
KQNKQGANSRPVNQTPPPEGEKLHSDSGI;

(SEQ ID NO: 50)
QNKQGANSRPVNQTPPPEGEKLHSDSGI;

(SEQ ID NO: 51)
NKQGANSRPVNQTPPPEGEKLHSDSGI;

(SEQ ID NO: 52)
KQGANSRPVNQTPPPEGEKLHSDSGI;

(SEQ ID NO: 53)
QGANSRPVNQTPPPEGEKLHSDSGI;

(SEQ ID NO: 54)
GANSRPVNQTPPPEGEKLHSDSGI;

(SEQ ID NO: 55)
ANSRPVNQTPPPEGEKLHSDSGI;

(SEQ ID NO: 56)
NSRPVNQTPPPEGEKLHSDSGI;

(SEQ ID NO: 57)
SRPVNQTPPPEGEKLHSDSGI;

(SEQ ID NO: 58)
RPVNQTPPPEGEKLHSDSGI;

(SEQ ID NO: 59)
PVNQTPPPEGEKLHSDSGI;

(SEQ ID NO: 60)
VNQTPPPEGEKLHSDSGI;

(SEQ ID NO: 61)
NQTPPPEGEKLHSDSGI;

(SEQ ID NO: 62)
QTPPPEGEKLHSDSGI;

(SEQ ID NO: 63)
TPPPEGEKLHSDSGI;

(SEQ ID NO: 64)
PPPEGEKLHSDSGI;

(SEQ ID NO: 65)
PPEGEKLHSDSGI;

(SEQ ID NO: 66)
PEGEKLHSDSGI;

(SEQ ID NO: 67)
EGEKLHSDSGI;

(SEQ ID NO: 68)
GEKLHSDSGI;

(SEQ ID NO: 69)
EKLHSDSGI;

(SEQ ID NO: 70)
KLHSDSGI;

(SEQ ID NO: 71)
LHSDSGI;

(SEQ ID NO: 72)
HSDSGI;

(SEQ ID NO: 73)
SDSGI;

(SEQ ID NO: 74)
DSGI;

SGI;

GI;
and

I.
```

EXAMPLE 3

Role of Bcl-2 in Promoting $p75^{NTR}$ Mediated Death Signalling

As the inventors had shown that the death of dorsal root ganglia (DRG) sensory neurons in vitro and in vivo, was, at least in part, mediated by $p75^{NTR}$, $p75^{NTR}$ was over-expressed in these cells by microinjecting rat p75NTR cDNA expressing plasmid into the nucleus of mouse sensory neurons. These were cultured in the presence of the L1F to prevent neural death not linked to $p75^{NTR}$ mechanisms. It was found that the expression of the rat $p75^{NTR}$ could be detected by surface immunofluorescence within 24 hours of injection. The injected neurons were observed over a 48 hour period and the viability was assessed. It was found that within the first 16 hours, a significantly higher number of $p75^{NTR}$ plasmid injected neurons had died compared to neurons injected with control plasmids β-galactosidase, or a truncated $p75^{NTR}$ protein lacking the entire cytoplasmic domain ($p75^{NTR}$nc). It was found that $p75^{NTR}$-mediated neural death occurred later in the experiment similar to Fas/TNF-induced rapid cell death. Since both full-length $p75^{NTR}$ and $p75^{NTR}$ nc protein showed a similar level of expression after injection, this indicates that the cytoplasmic domain of $p75^{NTR}$ is required for death signalling. This was expected since the cytoplasmic tail contains a sequence with homology to the Fas/TNFR "death domain" [9].

The inventors next examined whether deletion of the "death domain" also abolished the ability of $p75^{NTR}$ to kill. It was found that the neural death observed after expression of $p75^{NTR}$ with a truncated cytoplasmic tail ($p75^{NTR}$tr) was equivalent to the full-length $p75^{NTR}$ protein. This demonstrated that the "death domain" was not required for $p75^{NTR}$ killing and, since the $p75^{NTR}$ death domain has recently been shown to have a different tertiary structure to TNFR family death domain and does not self-associate in vitro, it suggests that the p75$^{NTR}$ "death domain" may not normally function to induce death. Together, these results predict that an alternative pathway involving proteins other than "death domain" adapter proteins, such as TRADD and FADD, is responsible for p75$^{NTR}$-mediated killing.

The Bcl-2 family of proteins is involved in mediating apoptotic signalling pathways, and can homodimerise or heterodimerise with other family members. Bcl-2 and Bcl-xL are well characterised inhibitors of stress-induced apoptosis, JNK activation and neural death due to growth-factor limitation. However, both are poor inhibitors of Fas and TNFR mediated apoptosis. As it had been shown previously that high levels of Bcl-2 or Bcl-xL blocked neural cell death in a variety of models, the inventors examined whether over-expression of these proteins could block the death induced by p75$^{NTR}$.

The inventors found that over-expression of Bcl-xL protected neurons against p75$^{NTR}$-induced death, supporting the hypothesis that p75$^{NTR}$ signals through an alternative pathway to TNFR-induced apoptosis. In contrast, while Bcl-2 overexpression alone had no effect on cell survival in the presence of L1F, Bcl-2 in combination with p75$^{NTR}$ over-expression, surprisingly, induced a significant increase in neural death above that seen with p75$^{NTR}$ over-expression alone. Bcl-2 in combination with p75$^{NTR}$nc did not cause significant cell death and furthermore, the cell death observed with p75$^{NTR}$ and Bcl-2 over-expression was totally ablated if the cells were cultured in NGF. Bcl-2 was able to protect against neural death induced by NGF withdrawal, but not withdrawal of L1F. Thus, at the same expression levels in the same neural population, Bcl-2 was able to prevent or enhance neural cell death depending on the nature of the death signal.

These results are surprising since Bcl-2 has previously been shown to have similar actions to Bcl-xL in almost all cell-death systems. To determine whether the paradoxical effect of Bcl-2 on p75$^{NTR}$-induced killing was related to its known anti-apoptotic activity, Bcl-2 proteins with inactivating point mutation, G145E, in the "Bcl-2 Homology" BH1 domain and W188A in the BH2 domain were utilised. Like wildtype Bcl-2, expression of either Bcl-2 mutant alone did not effect neural survival. In combination with p75$^{NTR}$ expression, the enhanced killing effect seen with Bcl-2 co-expression was abrogated by the G145E mutation, even though the proteins were expressed to comparable levels. Thus, an intact BH1 homology region is required for the death promoting activity of Bcl-2.

Mutation of the equivalent G 138 residue in Bcl-xL results in a conformational change between a-helices 4 and 5, disrupting access to the hydrophobic cleft formed by BH1, BH2 and BH3 domains. Therefore, the molecular mechanism by which Bcl-2 participates in the p75$^{NTR}$ killing pathway may be dependent on interactions either directly with the BH domains or with the hydrophobic cleft, as indicated with experiments using the W188A mutation. Co-expression of p75$^{NTR}$ with the Bcl-2 W188A protein not only abrogated the increased p75$^{NTR}$ killing but, more importantly, protected neurons from any p75$^{NTR}$-induced death, reminiscent of that seen with Bcl-xL. These experiments suggest that the conformation of the Bcl-2 protein is integral to the opposing functions observed herein.

The inventors had observed that DRG neurons isolated from newborn mice depleted for p75$^{NTR}$ were less susceptible to NGF withdrawal, as is the case with sympathetic neurons, when compared to neurons from wildtype mice. This is indicative of absent or delayed naturally occurring cell death observed in these mice. The inventors attempted to induce cell death in p75$^{NTR}$ "knock out" DRG neurons by re-introducing p75$^{NTR}$ expression. Surprisingly, apoptosis was not induced by re-expression into "knock out" DRG neurons, the inventors found that neural death was significantly increased under these conditions. This implicated an absolute requirement for Bcl-2 in mediating p75$^{NTR}$ killing.

The inventors tested, therefore, whether high endogenous Bcl-2 levels might be necessary for successful p75$^{NTR}$-mediated killing in normal neurons by assaying p75$^{NTR}$ killing in Bcl-2 depleted cells. Endogenous Bcl-2 was down regulated by antisense as previously described. When the Bcl-2 antisense plasmid was injected at the same time as p75$^{NTR}$ plasmids no diminishment in the death signal was seen. If, however, the Bcl-2 antisense was microinjected first (to give time to reduced Bcl-2 production and deplete endogenous Bcl-2; and then a day later the p75$^{NTR}$ or p75$^{NTR}$nc constructs were microinjected, there was no difference in survival between p75$^{NTR}$ and p75$^{NTR}$nc expressing neurons, strongly suggesting that endogenous Bcl-2 is required for p75$^{NTR}$ killing effects. To confirm this observation, the inventors isolated neurons from newborn Bcl-2 "knock out" mice (an heterozygous line of mice containing a disrupted Bcl-2 gene) and their wild-type litter mates and compared the effect of p75$^{NTR}$ over-expression with control plasmid p75$^{NTR}$ It was found that the neurons isolated from Bcl-2 deficient mice were significantly protected from p75$^{NTR}$ killing, showing a 56.9% (n=3) reduction in death compared wildtype neurons, supporting the hypothesis that endogenous Bcl-2 is required for p75$^{NTR}$ killing.

Bcl-2 has previously been observed to increase cell death when highly expressed both in vitro and in vivo when expressed at high levels as a transgene, causing increased apoptosis in the brain under a neuron specific promoter, or in photoreceptor cells when expressed specifically under a rhodopsin promoter. Thus, it is possible that the high level of Bcl-2 is able to "prime" the death pathway such that an apoptotic stimulus via p75$^{NTR}$ results in rapid cell death. Bcl-2 and Bcl-xL when cleaved by caspases have also been shown to be capable of promoting apoptosis in vitro, with cells expressing non-cleavable mutant Bcl-2 and Bcl-xL proteins showing increased viability compared to cells expressing wildtype proteins. Cleavage of Bcl-2 is possible in this system, however, the Bcl-2 mutations which results in loss of death promoting activity, would not prevent cleavage of Bcl-2, indicating that cleavage of Bcl-2 would only be part of the mechanism by which Bcl-2 promotes killing. In addition, if cleavage was the dominant mechanism, Bcl-xL might be expected to act as a death signalling protein in this system.

To investigate whether the p75$^{NTR}$-Bcl-2 death-signalling cascade was dependent on caspase activation, inhibitors of caspases were employed. In the presence of zVAD, a nonspecific caspase peptide inhibitor, or after co-expression of modified crmA plasmids, designed to inhibit Group II caspases such as caspases 2 and 3, p75$^{NTR}$-mediated death was significantly reduced. Similarly, the modified crmA was able to block the killing induced by co-expression of p75$^{NTR}$ and Bcl-2. This indicates that p75$^{NTR}$ induced apoptosis is a caspase dependent pathway and that the mechanism by which Bcl-2 assists killing is through the same pathway.

EXAMPLE 4

Antagonsim of p75$^{NTR}$ Mediated Death Signalling

Figure 6:
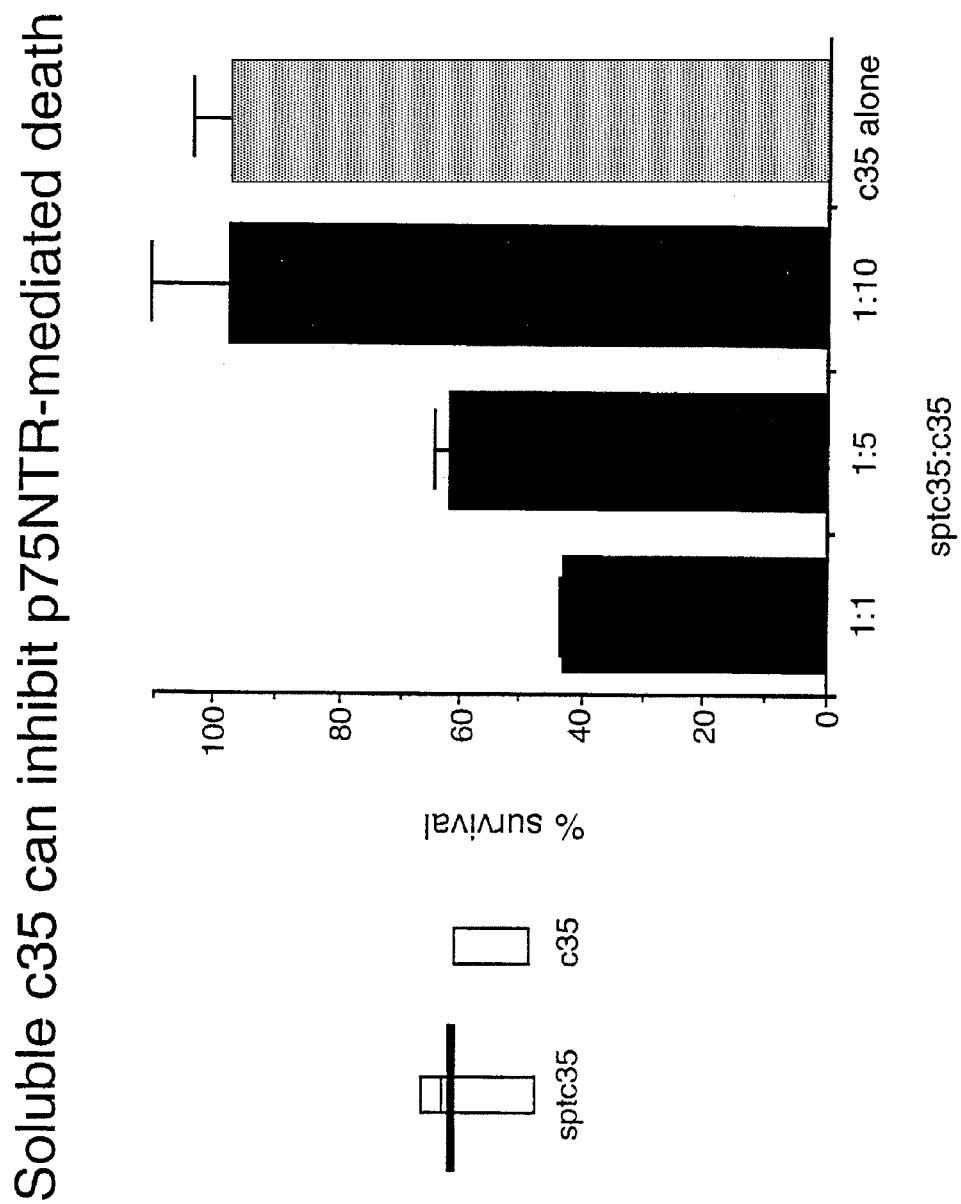
FIG. 6 is a graphical representation showing that soluble c35 inhibits p75$^{NTR}$ mediated death signalling.
Figure 7:
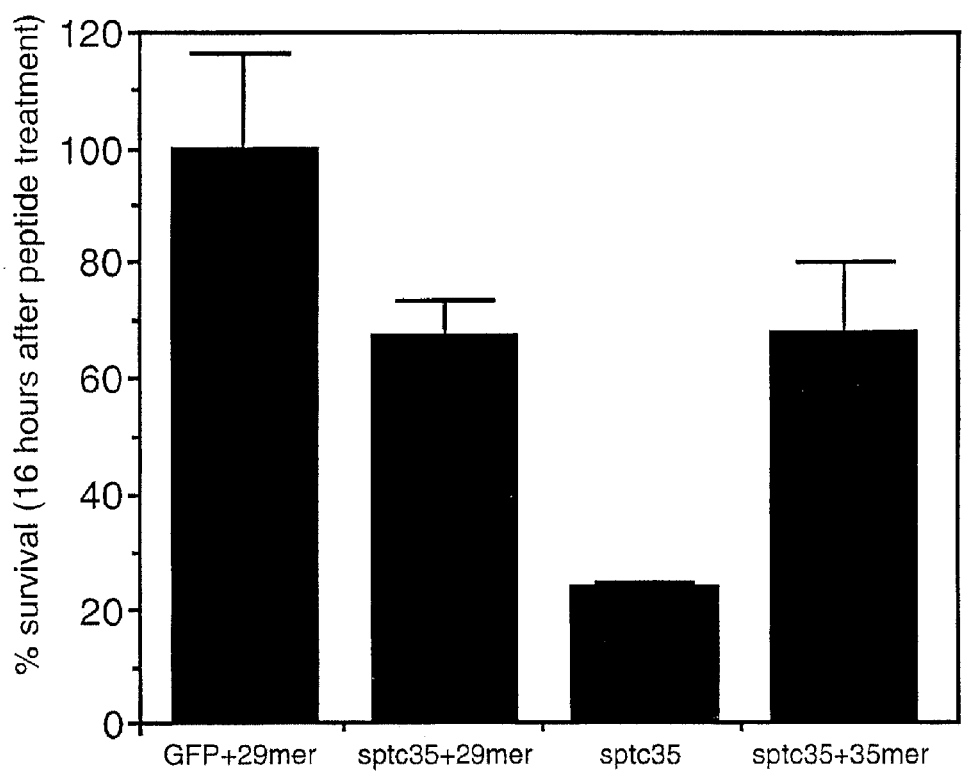
FIG. 7 is a graphical representation showing protection of membrane-bound killing-domain by a soluble 35 amino acid peptide and a soluble 29 amino acid peptide. The cells were subjected to microinjection of sptc35 or GFP followed minutes later by either peptide c35 or the 29 mer peptide.

FIG. 6 shows that soluble c35 (35mer) (SEQ ID NO:7 and SEQ ID NO:8) protects cells from death signalling in a dose-dependent manner against membrane bound c35. Furthermore, the 35 mer when expressed from a genetic construct, protected Schwann cells against NGF-induced death. c35 when expressed in soluble form can also protect cells against membrane bound c35. The inventors show in FIG. 7 that soluble c35 can also protect against membrane-linked, expressed c35. A truncated form of c35, a 29 mer, (SEQ ID NO:11 and SEQ ID NO:12) also protected against membrane-bound c35, when in soluble form.

Figure 8:
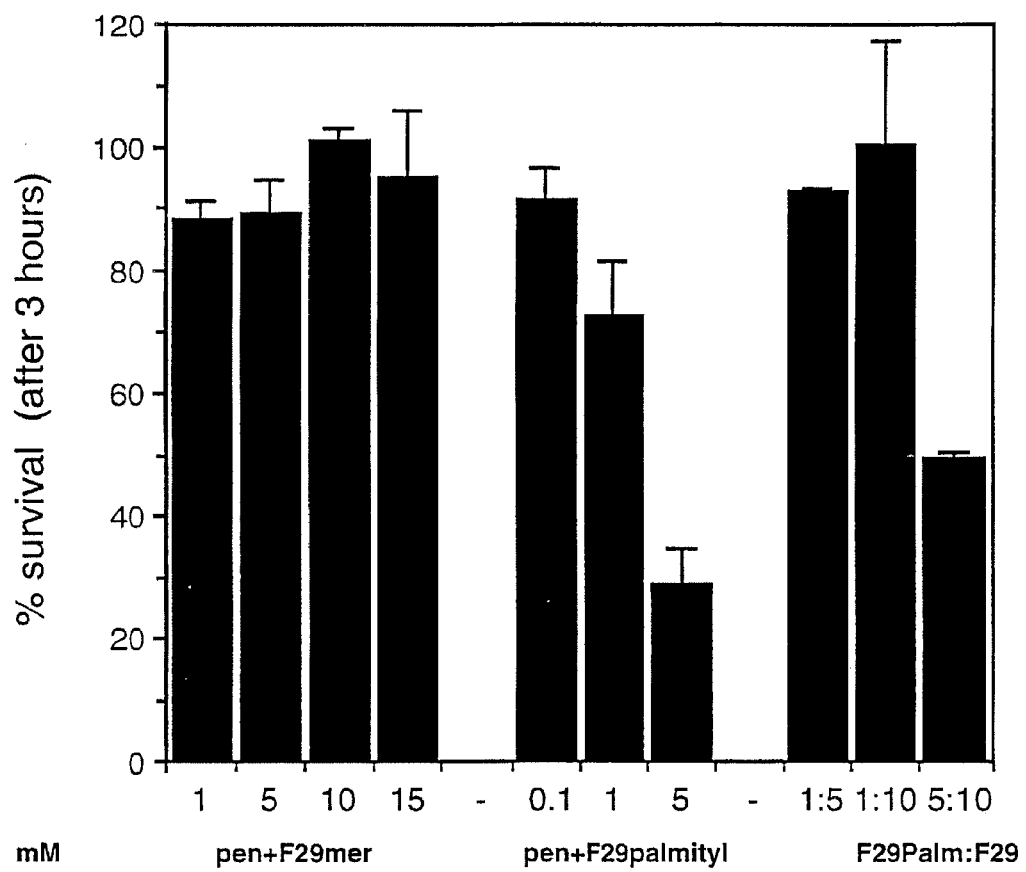
FIG. 8 is a graphical representation showing that peptide 29 which has a palmitoyl group at the membrane (amino) end and which facilitates association with the membrane mediates to cell death. In contrast, the soluble 35 amino acid molecule tends to protect the cells. F, Fluoro tagged; pen, penetratin.

FIG. 8 shows that the 29 mer with a palmitoyl group at the membrane (amino) end resulted in cell death. The palmitoylation links the peptide to the plasma membrane. This membrane-linked 29 mer leads to cell death whereas its soluble form protects cells against p75$^{NTR}$-mediated death signalling.

EXAMPLE 5

Effects of Palmitoylation

Figure 9:
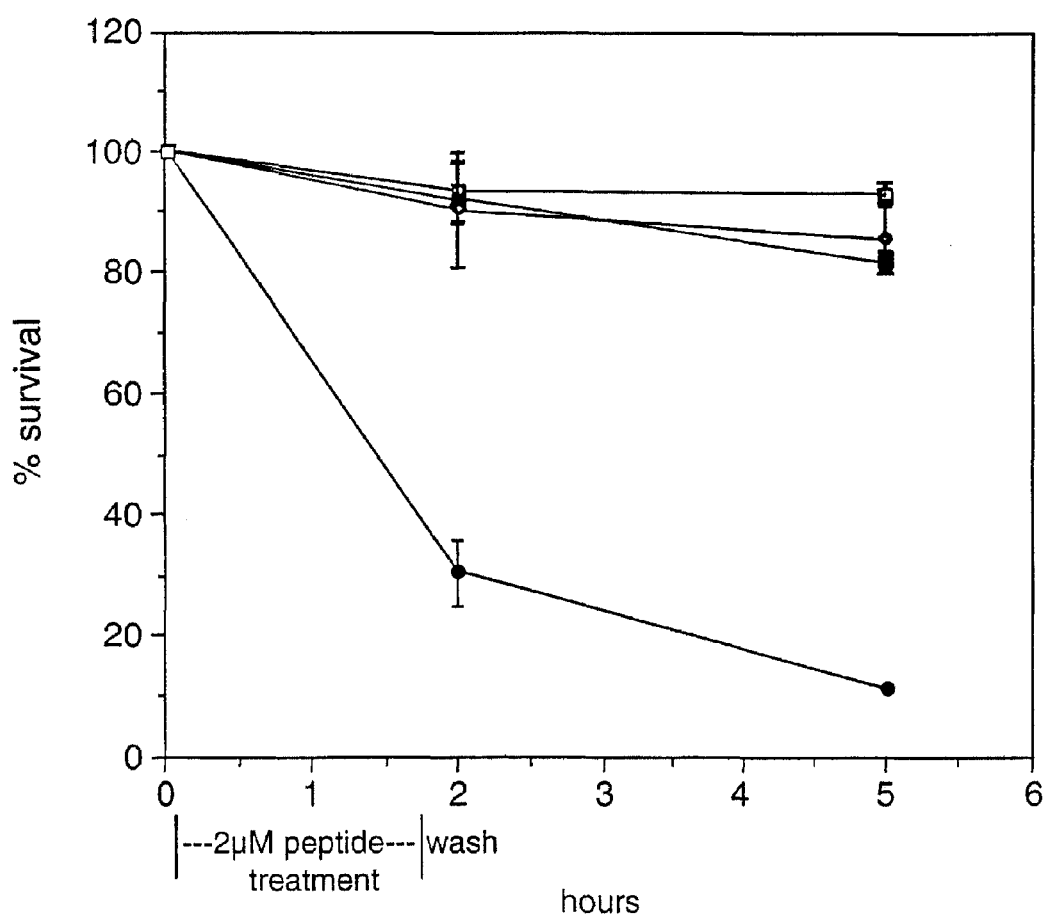
FIG. 9 is a graphical representation showing the palmitoylated 29 mer fused to penetratin mediates specific killing whereas non-palmitoylated 29 mer blocks cell death. Cells were treated with 2 μM peptide for 1-2 hours then washed. pen, penetratin; F29, 29 mer; Palm, palmitoylation.

FIG. 9 shows the effects of palmitoylated 29 mer (fused to penetratin) on mediating cell death. Cells were washed with peptide (2 μM) for approximately 110 minutes and the cells were then washed. Controls included penetratin-fused 29 mer, palmitoylated penetratin-fused 29 mer palmitoylated penetratin-fused gp130 and penetratin alone. Palmitoylated, penetratin fused 29 mer mediated significant cell death.

EXAMPLE 6

Passage Across Blood Brain Barrier

The ability for peptides to cross the blood brain barrier is tested using fluorescence-linked peptides injected intraperitoneally into mice. The peptides may be fused to penetratin or fused or associated with the TAT protein from HIV (18).

EXAMPLE 17

Animal Models

Peptides are delivered with penetratin or TAT (18) to various animal models for neurodegenerative diseases. The animal models used include:

| Animal Model | Disease |
|---|---|
| Axotomy of newborn rat sensory neurons | Peripheral neuropathies |
| Axotomy of newborn rat motor neurons (SOD1 mice: 86SJL-TgN [SOD1- G93A] 1 Gurd1) | Motor neuron disease |
| Ischemia of adult rats | Stroke |
| Experimental allergic encephamylitis and optic nerve axotomy [19] | Multiple sclerosis |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A method for reducing $p75^{NTR}$-mediated cell death in a mammalian neural cell, comprising contacting said cell with an effective amount of a soluble polypeptide that antagonizes $p75^{NTR}$ receptor, wherein said polypeptide comprises the amino acid sequence of SEQ ID NO:12, or a contiguous fragment thereof, wherein the fragment comprises at least 14 amino acids.

2. A method for reducing $p75^{NTR}$-mediated cell death in a mammalian neural cell, comprising contacting said cell with an effective amount of a soluble polypeptide that antagonizes $p75^{NTR}$ receptor, wherein said polypeptide comprises the amino acid sequence of SEQ ID NO:12.

3. The method of claim 2, wherein the mammalian neural cell is an isolated neural cell.

4. The method of claim 2, wherein the isolated neural cell is a dorsal root ganglia (DRG) or Schwann cell.

* * * * *